(12) United States Patent
Eggers et al.

(10) Patent No.: US 11,219,480 B2
(45) Date of Patent: Jan. 11, 2022

(54) APPARATUS, SYSTEM AND METHOD FOR EXCISION OF SOFT TISSUE

(71) Applicant: Hemostatix Medical Technologies, LLC, Bartlett, TN (US)

(72) Inventors: Philip E. Eggers, Dublin, OH (US); Brad Beale, Lakeland, TN (US); Jerry Van Eyck, Mill Creek, WA (US)

(73) Assignee: Hemostatix Medical Technologies, LLC, Bartlett, TN (US)

( * ) Notice: Subject to any disclaimer, the term of this patent is extended or adjusted under 35 U.S.C. 154(b) by 372 days.

(21) Appl. No.: 16/291,079

(22) Filed: Mar. 4, 2019

(65) Prior Publication Data
US 2019/0192209 A1    Jun. 27, 2019

Related U.S. Application Data

(62) Division of application No. 15/046,508, filed on Feb. 18, 2016, now abandoned.

(51) Int. Cl.
*A61B 18/08* (2006.01)
*A61B 18/14* (2006.01)
*A61B 18/00* (2006.01)

(52) U.S. Cl.
CPC ............ *A61B 18/08* (2013.01); *A61B 18/149* (2013.01); *A61B 2018/00178* (2013.01); *A61B 2018/00327* (2013.01); *A61B 2018/00607* (2013.01); *A61B 2018/00642* (2013.01); *A61B 2018/00702* (2013.01); *A61B 2018/00875* (2013.01);

(Continued)

(58) Field of Classification Search
CPC ... A61B 5/063; A61B 5/05–061; A61B 5/068; A61B 2018/1405
See application file for complete search history.

(56) References Cited

U.S. PATENT DOCUMENTS 5,308,311 A * 5/1994 Eggers ............... A61B 17/3211
                                                    600/28
5,480,397 A * 1/1996 Eggers ................ A61B 18/082
                                                    606/28

(Continued)

FOREIGN PATENT DOCUMENTS

DE         3826786 A1 * 2/1990 ......... A61B 17/3211

*Primary Examiner* — Linda C Dvorak
*Assistant Examiner* — Christine A Dedoulis
(74) *Attorney, Agent, or Firm* — Mueller Law, LLC; Jerry K. Mueller, Jr.

(57) ABSTRACT

Disclosed is a soft tissue excision apparatus having a handle and an elongated blade support member extending from the handle. The distal end of blade support member includes a first thermally conductive blade support arm and a second thermally conductive blade support arm. An electrically heatable blade is supported at and electrically isolated from the distal ends of the two thermally conductive blade support arms. A first electrically conductive lead extends from the proximal end of the thermally conductive blade support member to a first blade heater contact pad. A second electrically conductive lead extends from the proximal end of the thermally conductive blade support member to a second blade heater contact pad. First and second electrically conductive flexible leads extend from the proximal end of the thermally conductive blade support member to a controller.

14 Claims, 16 Drawing Sheets

(52) U.S. Cl.
CPC ............... *A61B 2018/1407* (2013.01); *A61B 2018/1412* (2013.01)

(56) References Cited

U.S. PATENT DOCUMENTS

| | | | | |
|---|---|---|---|---|
| 5,611,798 | A * | 3/1997 | Eggers | A61B 18/082 219/230 |
| 7,582,084 | B2 * | 9/2009 | Swanson | A61B 18/1206 606/40 |
| 2003/0229343 | A1 * | 12/2003 | Albrecht | A61B 18/14 606/45 |
| 2014/0276928 | A1 * | 9/2014 | Vanderpool | A61B 17/3468 606/129 |
| 2015/0032100 | A1 * | 1/2015 | Coulson | A61B 18/1233 606/35 |
| 2015/0080890 | A1 * | 3/2015 | Atwell | A61B 18/149 606/47 |

* cited by examiner

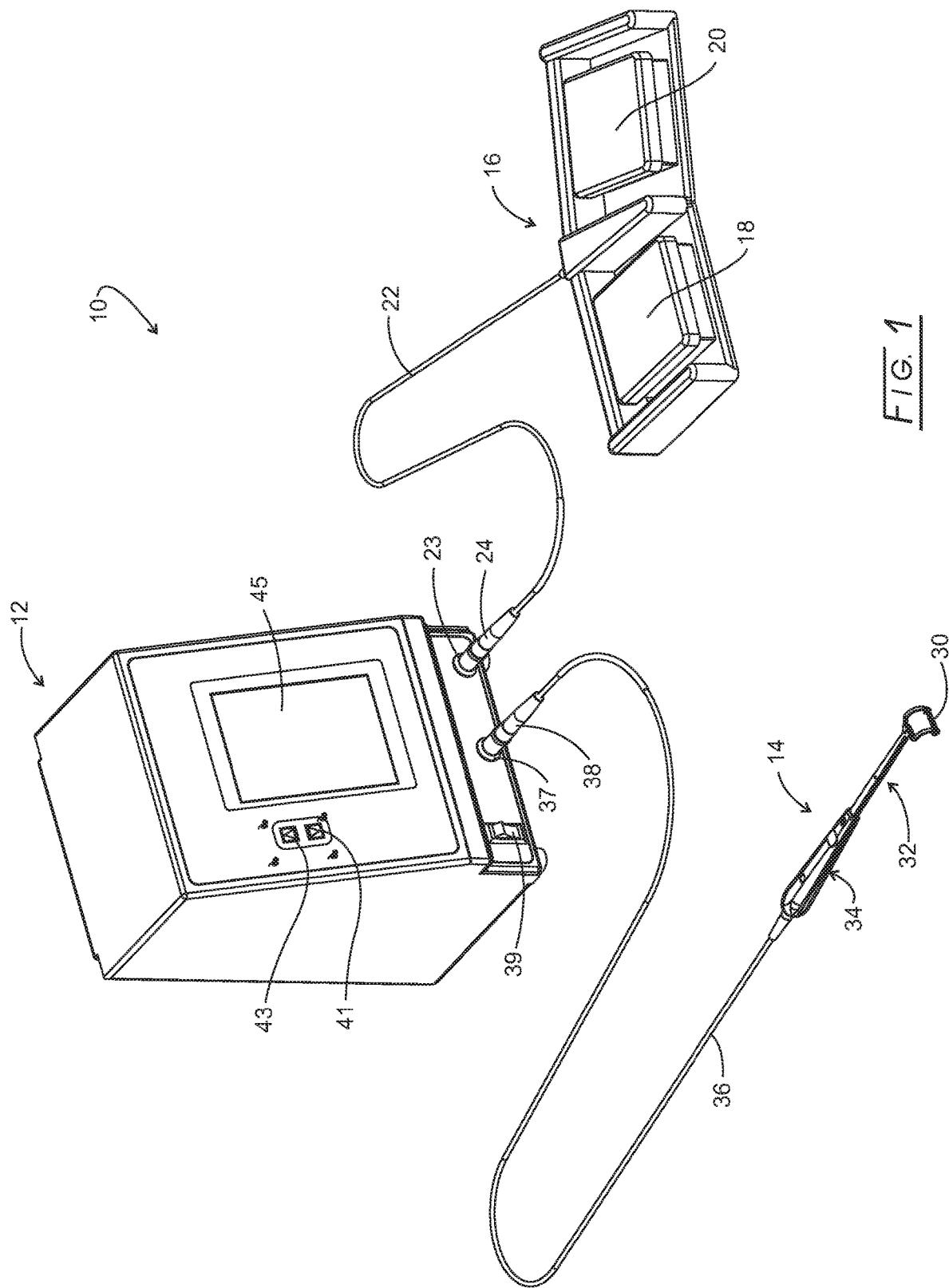

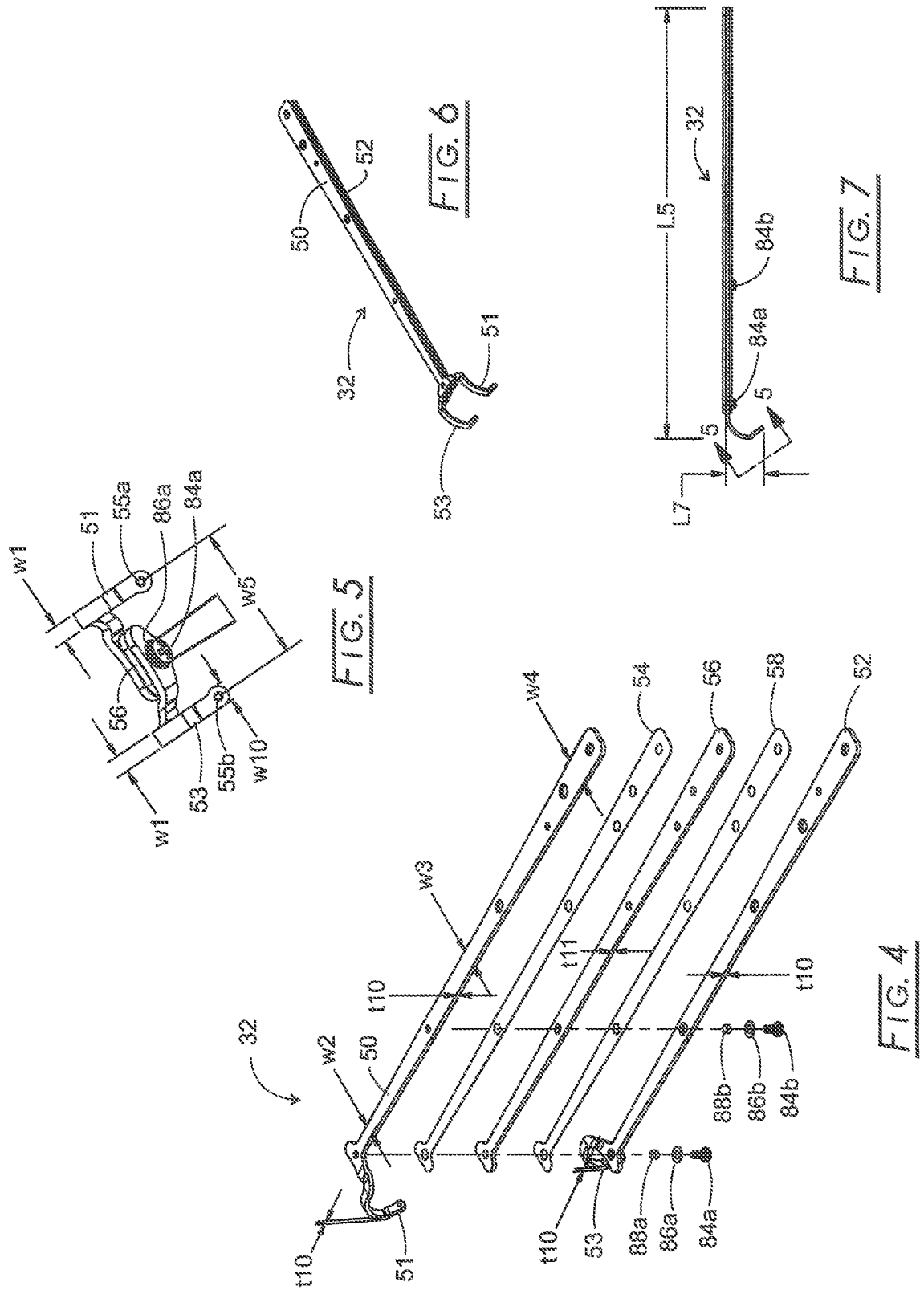

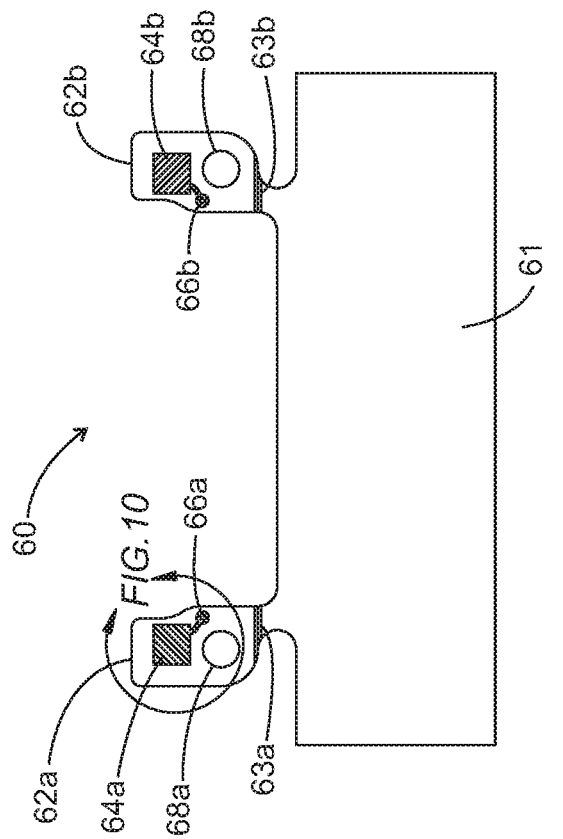
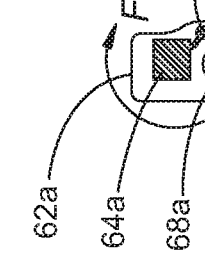
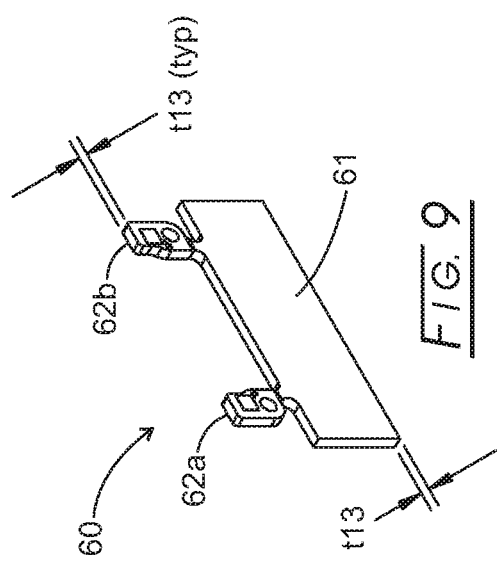
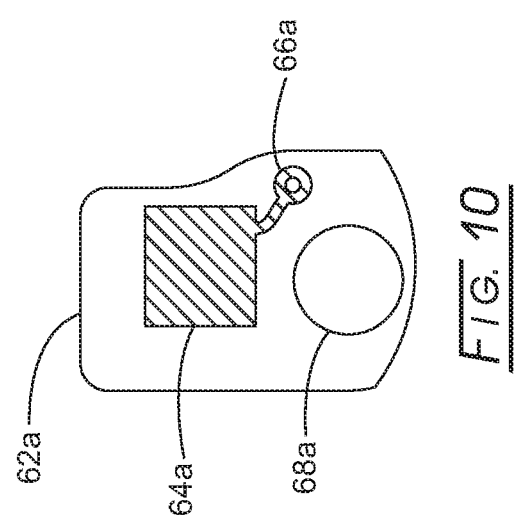
FIG. 8
FIG. 9
FIG. 10

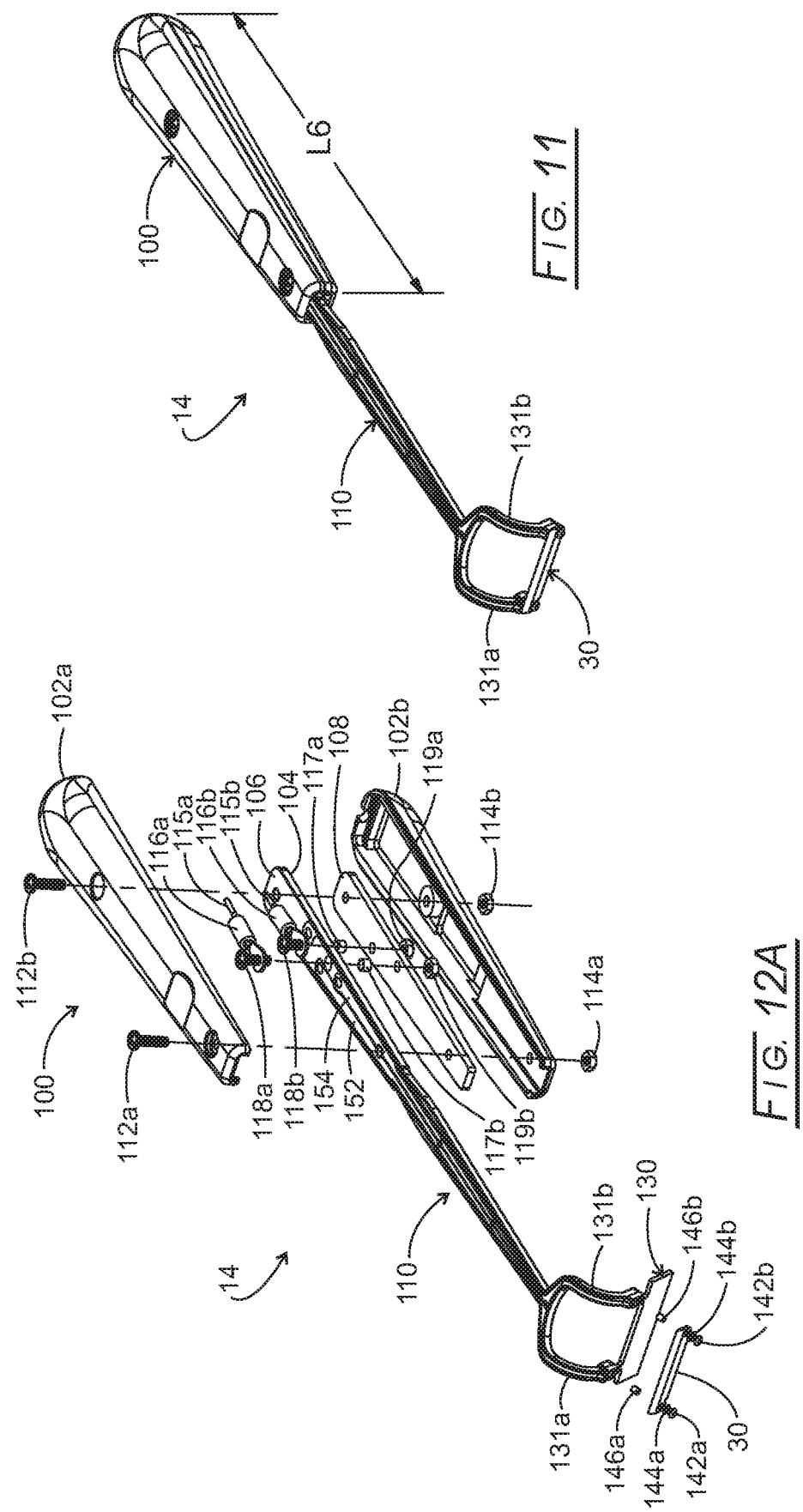

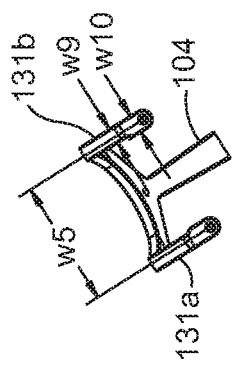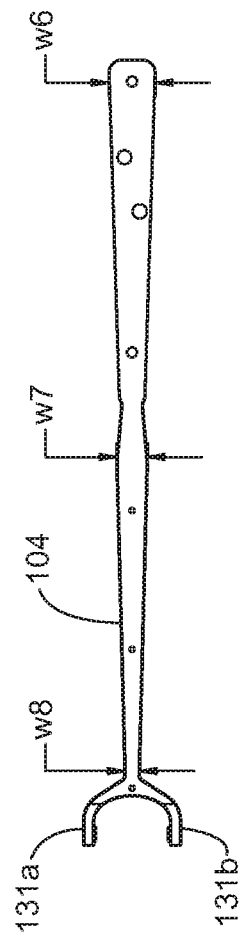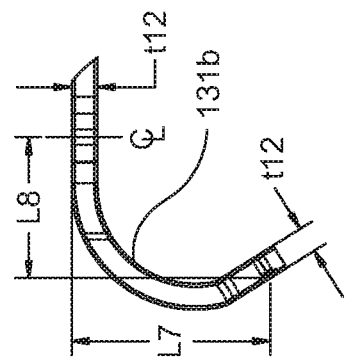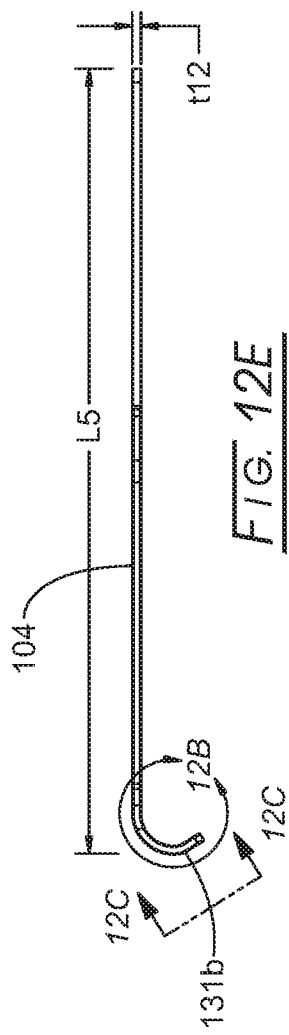

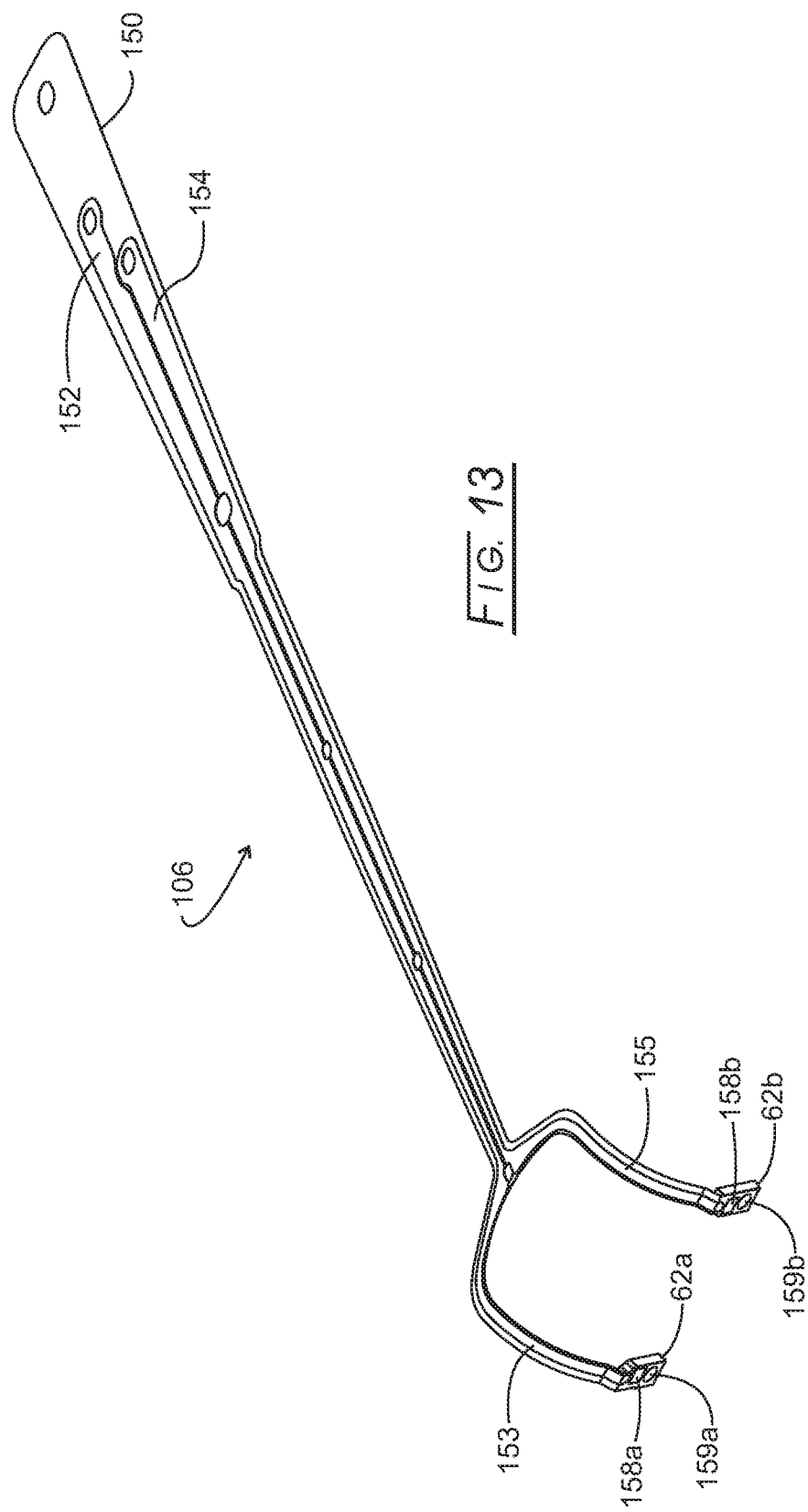

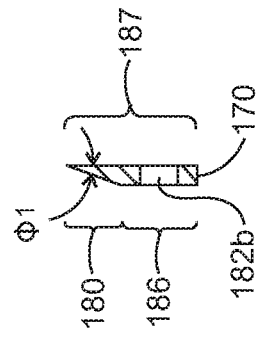
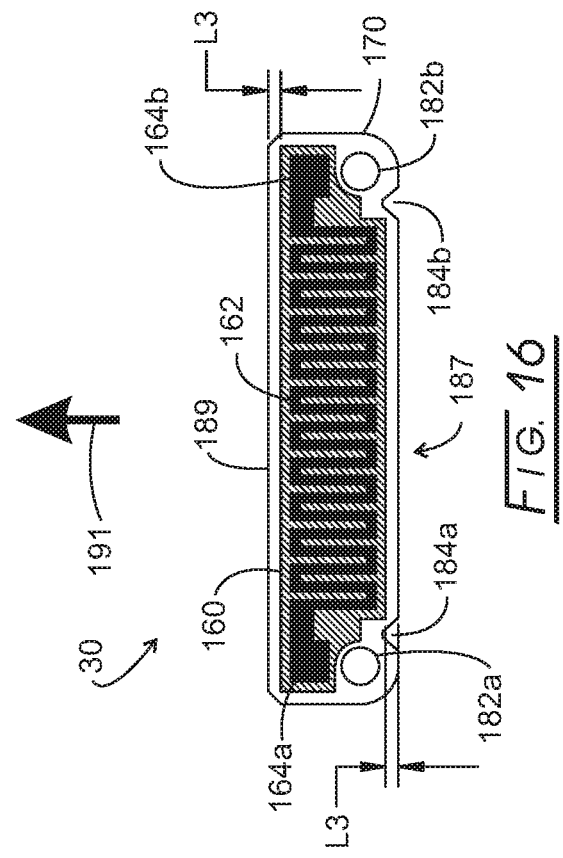
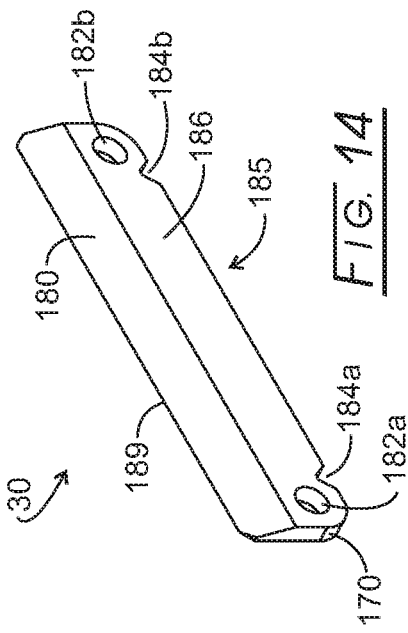
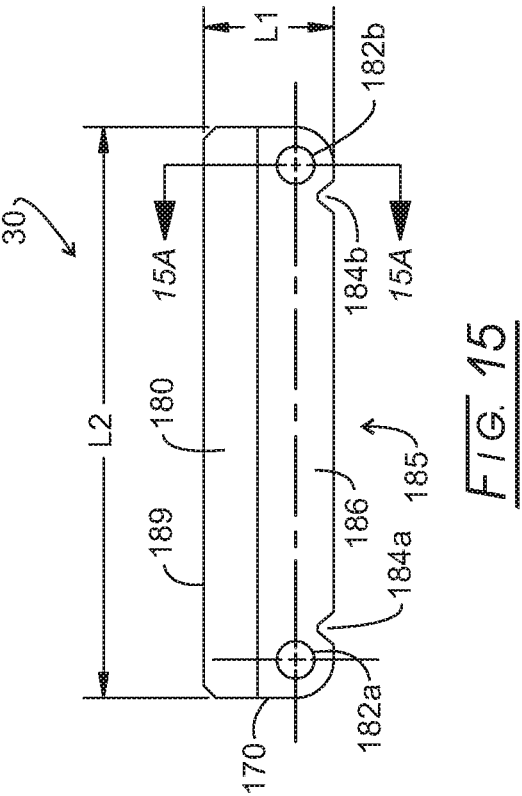

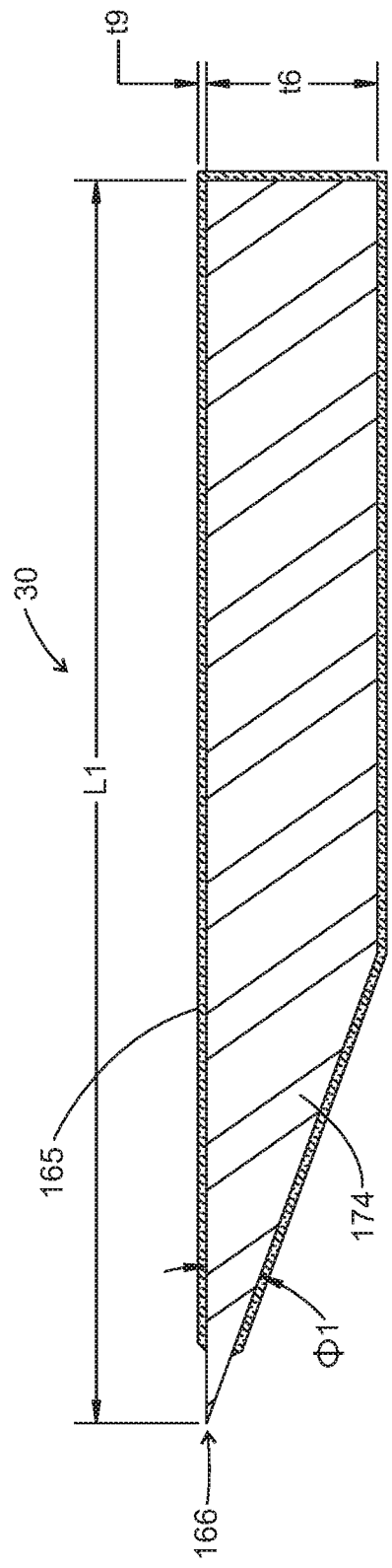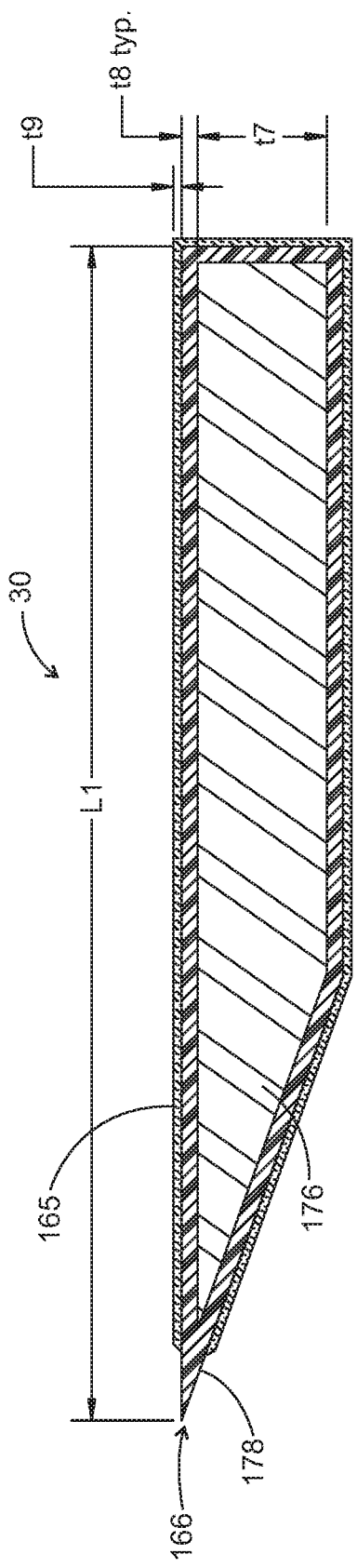

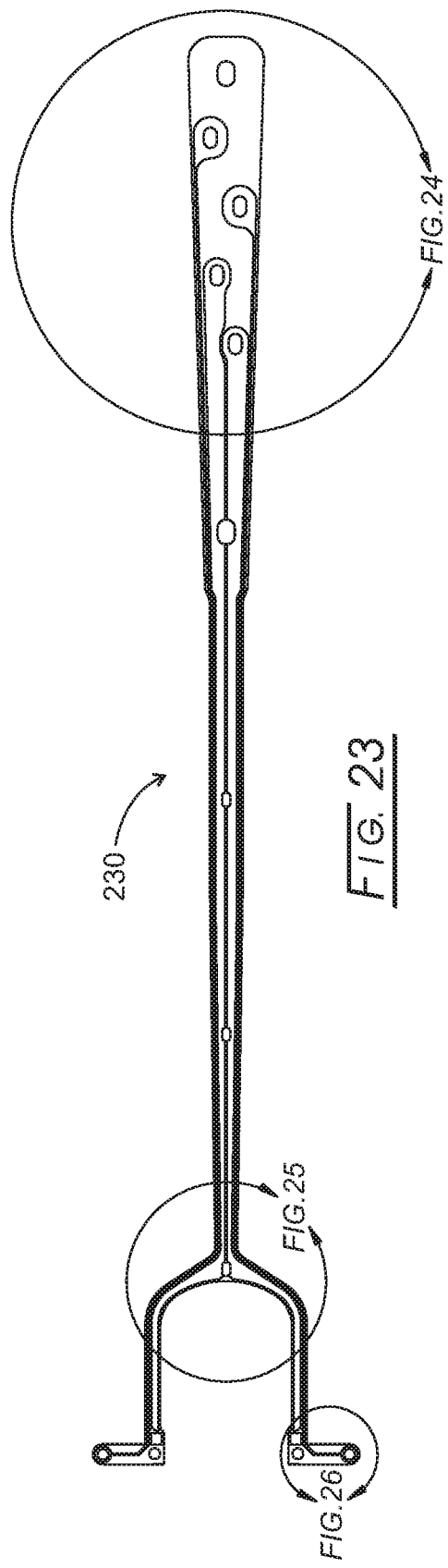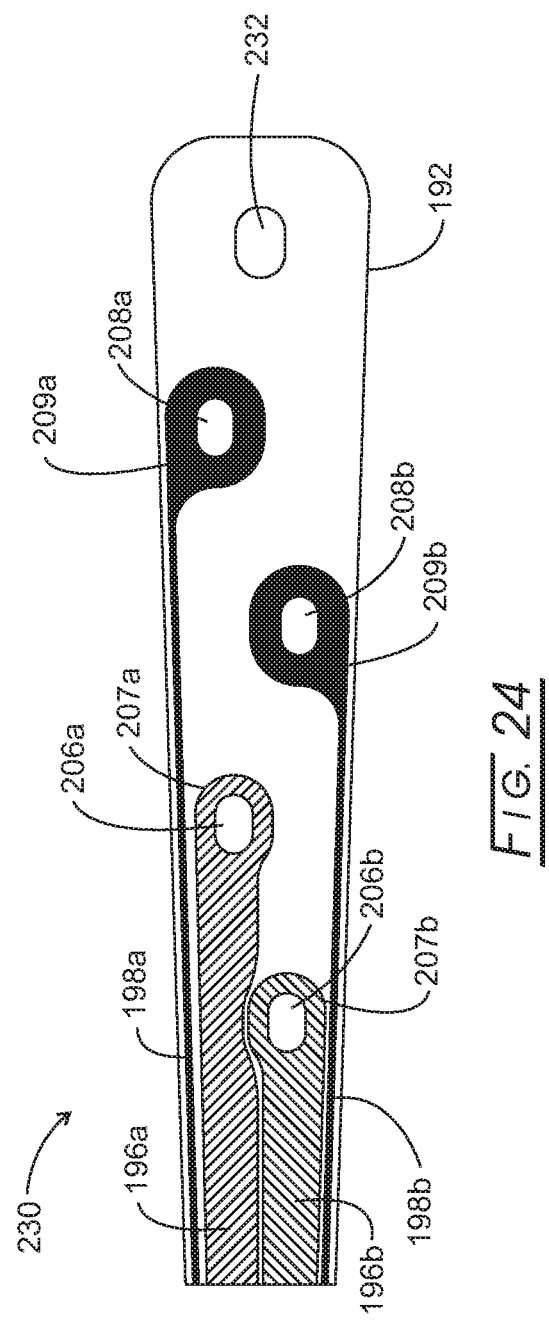

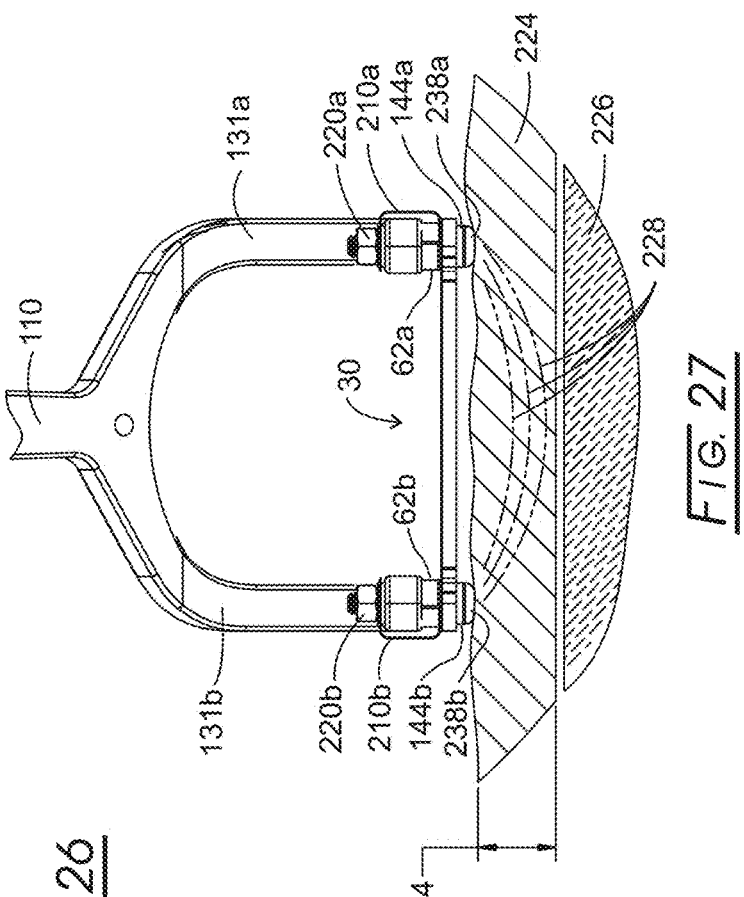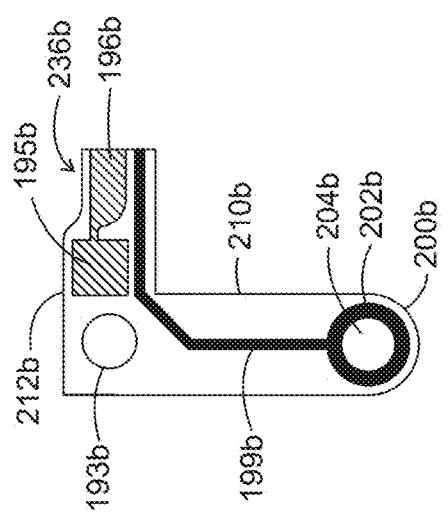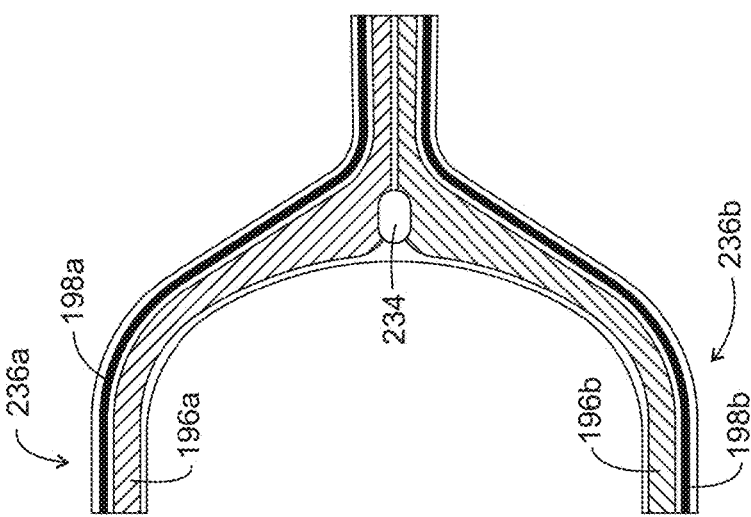

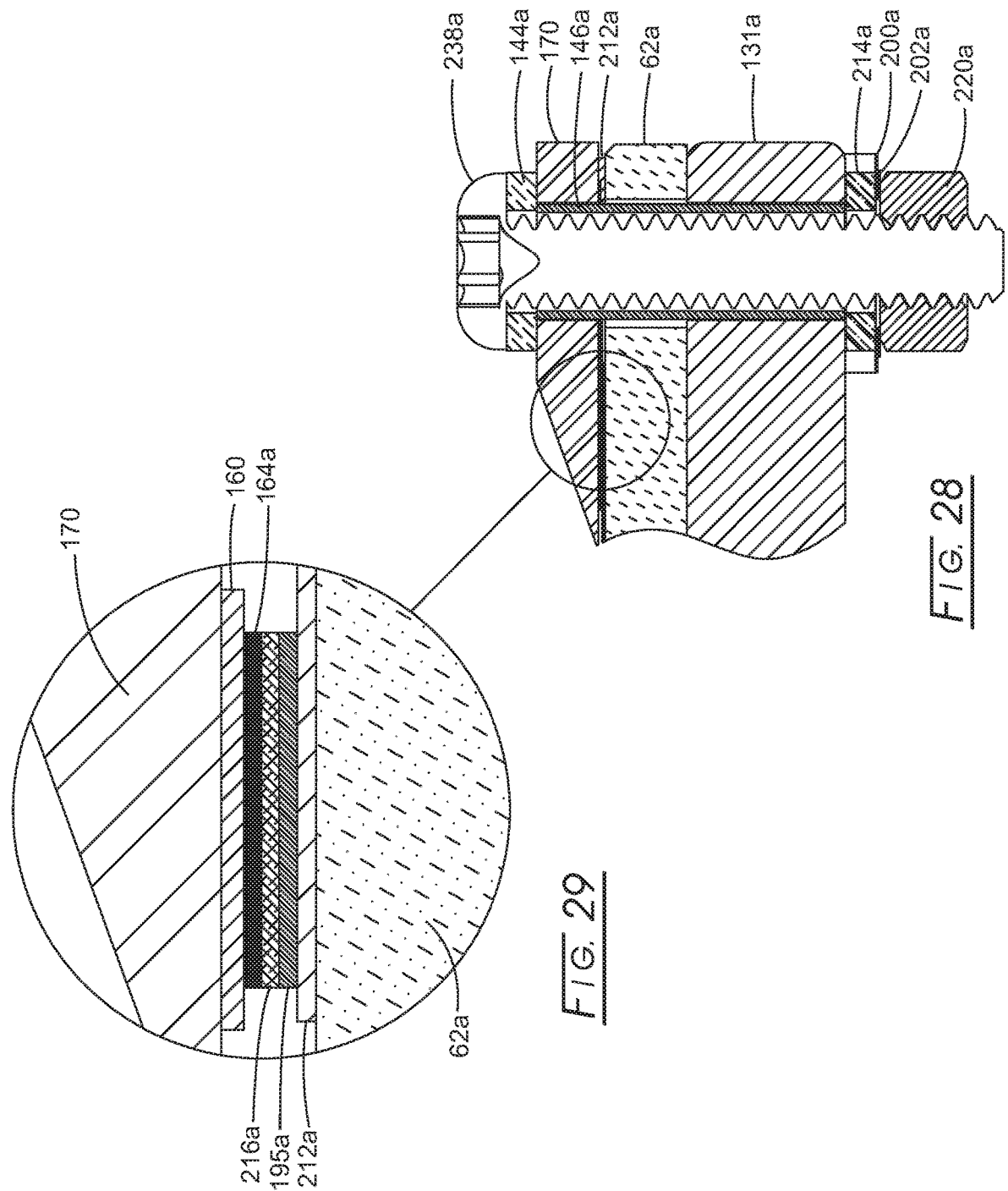

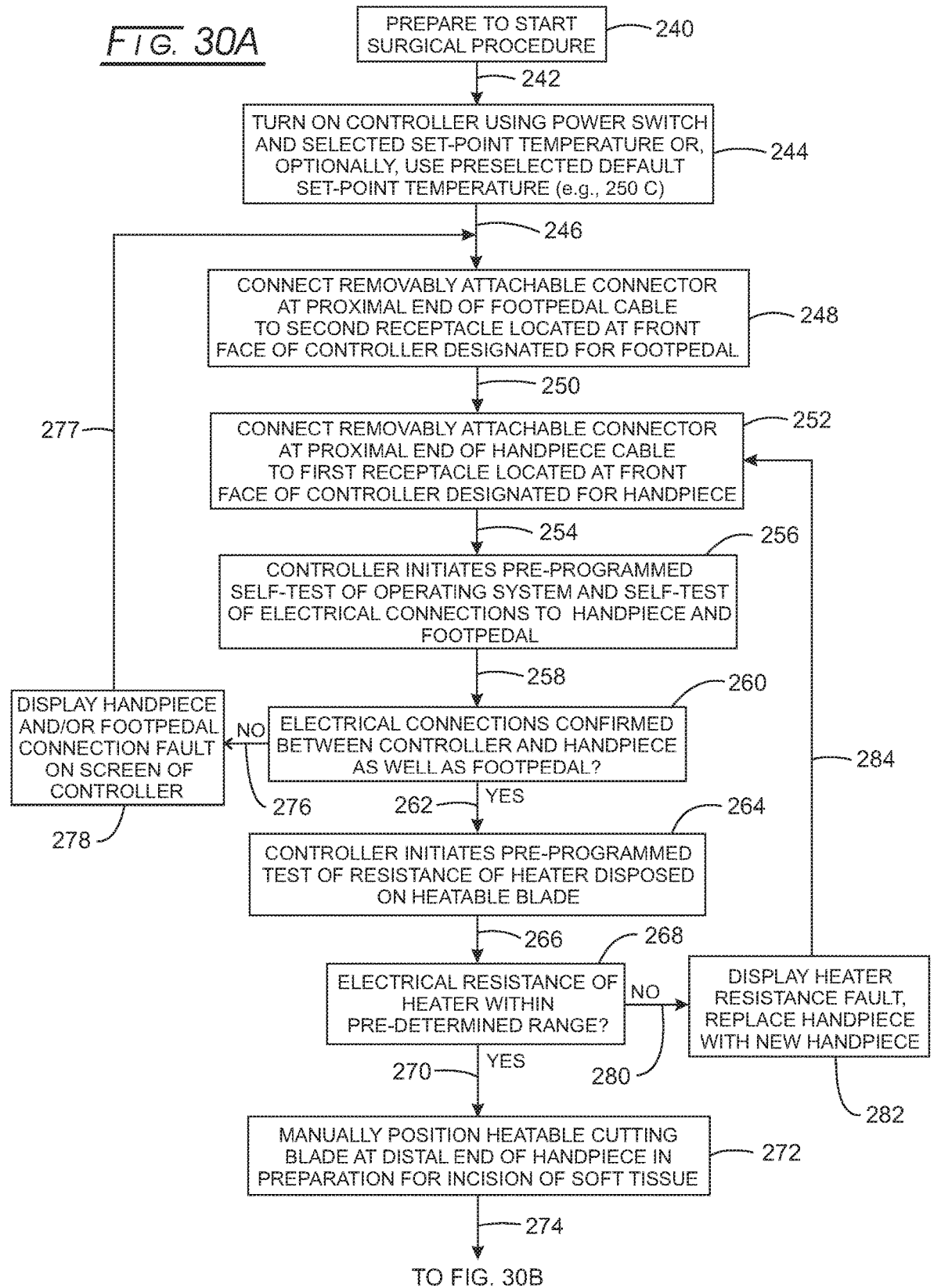

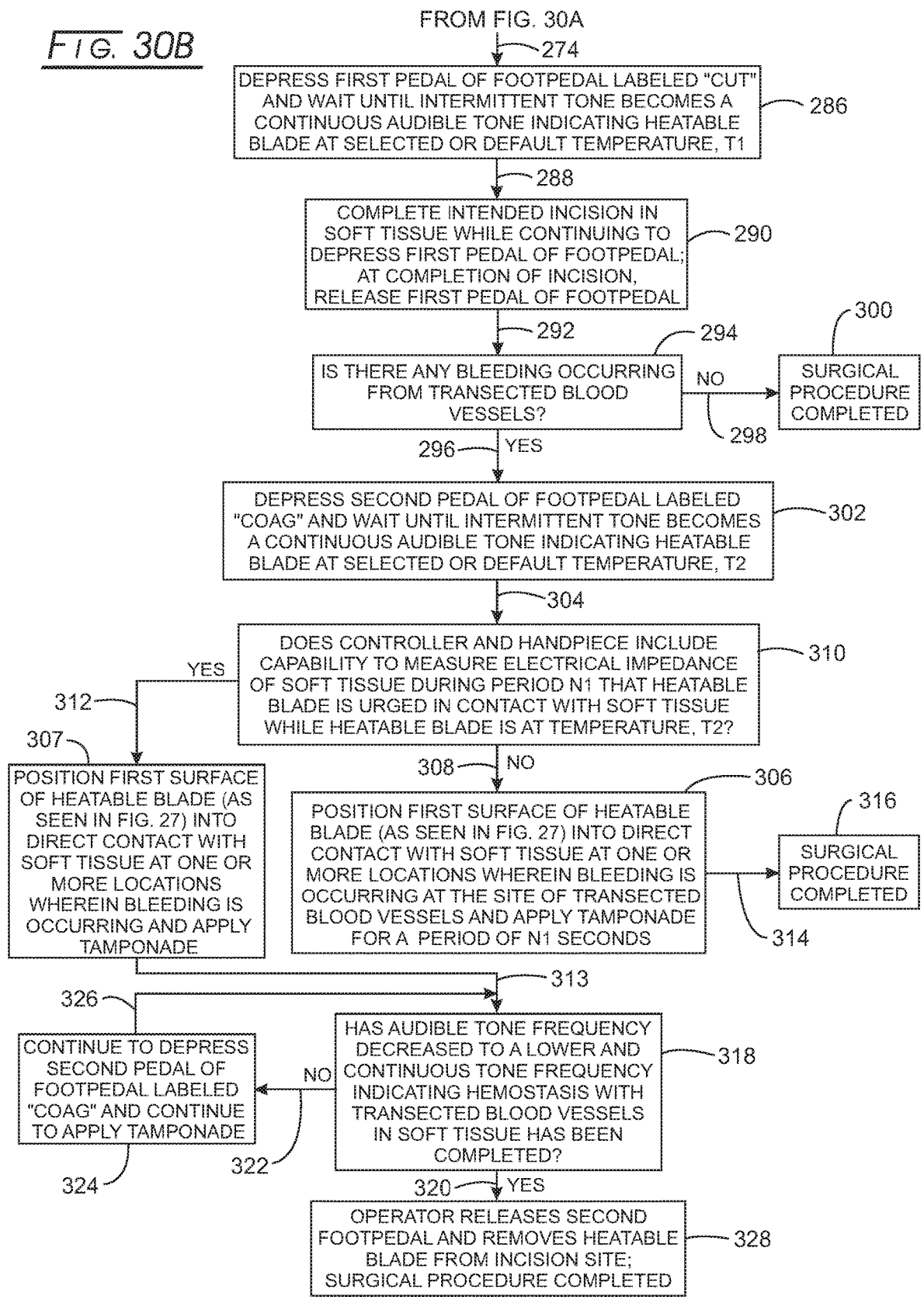

APPARATUS, SYSTEM AND METHOD FOR EXCISION OF SOFT TISSUE

CROSS-REFERENCE TO RELATED APPLICATIONS

This application is a division of application Ser. No. 15/046,508, filed Feb. 18, 2016, which application claimed benefit of provisional application 62/119,312, filed Feb. 23, 2015.

STATEMENT REGARDING FEDERALLY SPONSORED RESEARCH AND DEVELOPMENT

None

FIELD

The field of this disclosure is an apparatus, system and method for the incision of soft tissue in humans using a mechanically sharp blade with concurrent tissue heating to effect tissue incision with minimal bleeding. By way of example, the apparatus, system, and method of the present disclosure advantageously may be applied to surgical adenoidectomy and tonsillectomy.

BACKGROUND

The tonsils and adenoids are generally located in the back of the nose and throat. The tonsils and adenoids serve to collect and identify bacteria and/or viruses entering the body. Once identified, the immune system is activated to produce antibodies that target the invading bacteria and/or viruses to reduce or eliminate the bacteria and/or virus-induced infection. As bacteria and viruses are incorporated within the tonsils and adenoids, these tissues are able to deconstruct the bacteria and/or virus cells wall and release cellular contents to areas of the body that produce antibodies responsive to the cellular contents. Repeated inflammation of the tonsils and adenoids can overwhelm the capability of the tonsils and/or adenoids to deconstruct the bacteria and/or viruses incorporated within; thereby, resulting in bacterial and/or viral growth within the tissues of the tonsils and/or adenoids. The abnormal accumulation of bacteria and/or virus media within the tonsils and/or adenoids can induce repeated infections such as tonsillitis or ear infections. If antibiotic treatment fails to reduce or eliminate the level of growth of bacteria within the tonsils and/or adenoids, often leading to swelling to the point of airway obstruction, then excision of the tonsils and/or adenoids may be necessary.

The devices and techniques used for tonsillectomy and adenoidectomy procedures depend on the type and amount of tissue to be removed and surgeon preference. The tonsillectomy and adenoidectomy procedures routinely are performed together. A widely used method for tonsillectomy and adenoidectomy has utilized a sharp blade to effect mechanical excision of the tonsil and/or adenoid tissue. Although excision with a mechanically sharp blade provides for the precise removal of the intended tonsil and/or adenoid tissue it unavoidably results in heavy bleeding from the tissue bed underlying the tonsils and/or adenoids. Such heavy bleeding is staunched using tamponade (often combined with a coagulation inducing chemical agent) and/or the use of electrosurgery to locally heat and seal the excised open blood vessels. Although the use of electrosurgery to staunch the bleeding associated with tissue excision using a mechanically sharp blade serves to reduce intra-operative blood loss, it contributes to increased post-operative pain due to spread of the thermal injury to adjacent tissue and nerves due to the flow of electrosurgical currents beyond the surface of excision.

Another approach is the use of electrosurgery for both the excision of the adenoids and/or tonsils, as well as the post-excision application of electrosurgery-induced arcs to seal severed blood vessels and desiccate the underlying tissue bed to minimize further post-operative bleeding. Although the use of electrosurgery to staunch the bleeding associated with tissue excision using electrosurgical cutting serves to reduce intra-operative blood loss, it contributes to increased post-operative pain due to the spread of the thermal injury to adjacent tissue and nerves due to the flow of electrosurgical currents beyond the surface of excision.

Yet another approach is the volumetric removal of tonsil and/or adenoid tissue through the use of molecular disintegration of the targeted tissue. Although the use of molecular disintegration to volumetrically remove tissue and apply very localized tissue heating using a bipolar electrode configuration serves to reduce both bleeding and post-operative pain, it is unavoidably a much slower process than methods used to excise the tonsils and/or adenoids.

Prior art devices for the excision of tonsil and/or adenoid tissue are associated with disadvantageous post-operative bleeding, patient discomfort, and/or prolonged procedure times. It would, therefore, be advantageous to provide an apparatus, system, and method that provides for the precise and rapid excision of tonsils and/or adenoids while minimizing both intra-operative and post-operative bleeding, as well as minimizing post-operative pain.

BRIEF SUMMARY

The limitations of prior art devices for the excision of adenoid tissue are overcome by the apparatus, system, and method of the present disclosure comprising [a] a temperature controller, [b] a removably attachable flexible cable in electrical communication with both the temperature controller and a handpiece, and [c] a handpiece with a surgically sharp cutting edge, comparable to existing cold scalpels, combined with a heatable blade covered by a non-stick coating to minimize intra-operative and post-operative bleeding, as well as to minimize the avulsion of the sealing layer formed over transected blood vessels due to sticking of tissue to the heatable blade. Prior-art surgically sharp, heatable blades used for the incision and excision of mammalian tissue are disposed at the distal end of a support member or shank to minimize heat conduction into a hand piece and only the heated portion of the blade comes in contact with tissue. By way of example of prior-art surgically sharp, heatable blades used for the incision and excision of mammalian tissue, see U.S. Pat. Nos. 5,308,311 and 8,475,444, incorporated herein by reference.

In the present disclosure, a resistively heatable blade comprising a surgically sharp edge (i.e., incorporating a blade with a mechanically sharp cutting edge) is supported in close proximity at either end of the heatable blade by a first and second support arm of a curette. In order to avoid iatrogenic injury to healthy tissue adjacent to the site of the intended excision of adenoid tissue, the exposed surfaces of the first and second curette blade support arms must be maintained at a temperature below the threshold for thermal injury at all times during a surgical procedure. This critical requirement results from the fact that the intended use of an adenoidectomy curette in the confined region of the throat of the patient (the curette having a heatable blade operating at, by way of example, 250° C.) involves unavoidable contact of the blade support arms with adjacent vital tissue that should not be injured.

By way of example, the surgically sharp, heatable blade of the present disclosure may comprise a pre-sharpened surgical-grade metal blade substrate (e.g., heat treated and hardened martensitic stainless steel) coated with a first layer of electrically insulative material onto which is disposed a second layer of electrically resistive material exhibiting a large temperature coefficient of electrical resistance (e.g., copper or silver heater material) to form an electrically resistive heating element. The electrically resistive heating element section (e.g., a serpentine pattern of electrically resistive material) is disposed on one side of the central portion of the blade and terminated by first and second heater contact pads at either end of the heating element section. The first and second contact pads are positioned so that they are in electrical communication with corresponding first and second lead contact pads disposed on the first surface of first and second thermal barrier members. Third and fourth lead contact pads are disposed on the opposite sides of the first and second thermal barrier members, respectively, to enable electrical communication with the first and second blade support arms, respectively. The first and third lead contact pads on the first thermal barrier member are in electrical communication using a copper plated through hole commonly referred to as a via. Likewise, the second and fourth lead contact pads on the second thermal barrier member are in electrical communication using a copper plated through hole or via. Based on this example configuration and construction, the first and second thermal barrier members reduce the level of heat conduction from either end of the attached heatable blade to the first and second blade support arms. In addition to disposing a low thermal conductivity thermal barrier member between the heatable blade and the blade support arms to reduce the amount of heat conducted from the heatable blade to the distal ends of the first and second blade support arms, the cross-sectional area and thermal conductivity of the first and second support arms are selected to maximize the conduction of heat away from the distal ends of the blade support members. As a result of the high thermal conductance of the blade support arms, the heat conducted from the heatable blade is distributed over an extended length of the proximal sections of the blade support arms and their integral support shaft member, thereby maintaining the temperature of the exposed surfaces of the blade support arms below the temperature of irreversible thermal injury to tissue (e.g., preferably at a temperature below about 50° C. based on the expected duration of temperature contact during a surgical procedure).

In the above example, the temperature of the heating element is controlled to account for the significant difference in the rate of heat dissipation from the blade when it is in contact with air and tissue during tissue incision. The contact of the blade only with air represents a relatively low rate of heat dissipation due to the thermally insulative properties of air associated with conduction and convection heat transfer and relatively low rate of radiation heat transfer at the intended elevated blade temperatures. In contrast, the contact of the blade with tissue represents a significantly higher rate of heat dissipation than contact with air. To accommodate the avoidably large differences in heat dissipation during the intended use of the heatable blade during the intended surgical procedure, temperature feedback control is essential to maintain the blade within acceptable temperature range to avoid [a] excessively high temperatures when in contact with air (e.g., temperatures that could damage the non-stick coating and/or thermal barrier members) and [b] excessively low temperatures when in contact with tissue thereby limiting the intended transfer of heat to tissue at the cutting edge to seal incised blood vessels and thereby limit intra-operative and post-operative bleeding. The required temperature feedback control may be achieved in the present disclosure by any one of a number of feedback control processes or intrinsic temperature autoregulation mechanisms. By way of example but not limiting, temperature feedback control may be accomplished with the use of heating element comprising a material exhibiting a high temperature coefficient of resistance (e.g., heating element comprising copper, nickel, or silver). The controller uses the initially measured room-temperature resistance and known temperature coefficient of resistance of the heating element to determine the set-point heater resistance corresponding to the selected set-point temperature. This temperature control process is referred to hereinafter as resistance-feedback based temperature control.

In another embodiment of the present disclosure, the operating temperature of the heatable blade of the present disclosure may be controlled with the use of one or more temperature sensors (e.g., thermocouples) attached at one or more locations on heatable blade to regulate the application of power to one or more heater segments to maintain the user selected operating temperature. This temperature control process is commonly referred to hereinafter as temperature-sensor based feedback control. The use of temperature-sensor based feedback control may be combined with the use of a resistive heating element disposed on the mechanically sharp heatable blade or may be combined with the direct heating of the heatable blade by the flow of current through the length of the heatable blade. By way of example of current-flow induced resistive heating of the blade member, the blade may comprise a material exhibiting a high electrical resistivity and/or the application of a high frequency current to confine current flow to the surface layer of the blade, a heating effect commonly known as skin effect heating, as described in U.S. Pat. No. 4,701,587 and incorporated herein by reference. As specified in U.S. Pat. No. 4,701,587, skin effect heating can be enhanced through the use of a thin layer overlaying the blade member substrate that exhibits a higher electrical resistivity than the substrate blade member and the thin layer overlaying the blade member substrate may include a metal, metal alloy, metal ceramic, metal semiconductor, and/or metal oxide.

In yet another embodiment of the present disclosure, the operating temperature of the heatable blade of the present disclosure may be controlled using a ferromagnetic or ferrimagnetic blade member material or thin layer overlaying the blade member substrate that exhibits a Curie temperature selected to correspond to the pre-selected operating temperature of the heatable blade (e.g., 250° C.), thereby enabling the temperature to be controlled in a narrow range at or below the intrinsic Curie temperature of the blade member or the thin layer overlaying the blade member substrate. This temperature control process is referred to hereinafter as Curie temperature autoregulation based temperature control and is described in U.S. Pat. No. 4,701,587, which is incorporated herein by reference. The power source used in combination with Curie temperature autoregulation based temperature control commonly incorporates the use of a constant, high frequency current, typically ranging from, but not limited to, frequencies of about 5 megahertz to 24 gigahertz.

In yet another embodiment of the present disclosure, a ferromagnetic or ferrimagnetic blade member material or thin layer overlaying the blade member substrate may be selected so that the operating temperature of the heatable blade is below the Curie temperature of the ferromagnetic or ferrimagnetic blade member or thin layer overlaying the blade member substrate. In this alternative embodiment, a temperature sensor is positioned in thermal communication with heatable blade to measure, regulate, and maintain the temperature of heatable blade within a narrow range around a pre-selected set-point temperature. The heating current induced within the ferromagnetic or ferrimagnetic coating is a variable electrical current level to effect temperature feedback control of the heatable blade temperature. In this embodiment, the frequency ranges from about 4 megahertz to 24 gigahertz to induce skin effect heating wherein the current flow is predominantly confined to the surface or "skin" layer of the ferromagnetic or ferrimagnetic material.

In yet another embodiment of the present disclosure, first and second electrodes are disposed at the distal ends of the heatable blade and adjacent to the distal ends of the blade support arms to enable the intra-operative measurement of electrical impedance of the tissue located between the first and second electrodes. The level of electrical impedance of the tissue located between the first and second electrodes is measured using a current having a frequency of, but not limited to, 50 kilohertz to about 1 megahertz. The measured level of electrical impedance in the tissue located between the ends of and underlying the heatable blade is used to assess the level of tissue desiccation and associated hemostasis within the underlying tissue. The higher the level of measured electrical impedance between the first and second electrodes, the greater the extent of tissue desiccation and associated hemostasis. The measured electrical impedance of the tissue underlying the heatable blade can then be used to determine if a sufficient level of hemostasis has been attained to indicate the completion of the surgical procedure. In the event the measured level of electrical impedance of the underlying tissue is above some predetermined threshold, then the underside of the heatable blade surface adjacent to the tissue and operating at an elevated temperature (e.g., 250° C.) can continue to be urged against the underlying tissue to achieve a still greater degree of desiccation and associated hemostasis.

In yet another embodiment of the present disclosure, the first and second electrodes disposed at the distal ends of the heatable blade and adjacent to the distal ends of the blade support arms may be employed for both [a] the intra-operative measurement of electrical impedance of the tissue located between the first and second electrodes and [b] the conduction of high frequency current through the underlying tissue to effect resistive heating of the underlying tissue. This method of tissue heating by the passage of high frequency current directly through tissue is commonly known as bipolar electrosurgical heating and typically employs high frequency current whose frequency is at least 100 kilohertz and often, but not limited to, a frequency of less than 6 megahertz. Bipolar electrosurgical heating of tissue may be employed in combination with a resistively heatable blade (e.g., operating at a blade temperature of 250° C. using one of the aforementioned temperature feedback control mechanisms) or may be employed with a cold surgical blade to effect all of the necessary heating of the underlying tissue necessary to achieve the sealing of severed blood vessels and associated hemostasis.

The disclosure, accordingly, comprises the apparatus, system, and method possessing the construction, combination of elements, arrangement of parts and steps, which are exemplified in the following detailed description.

BRIEF DESCRIPTION OF THE DRAWINGS

For a fuller understanding of the nature and objects hereof, reference should made to the following detailed description taken in connection with the accompanying drawings.

FIG. 1 is an isometric representation of a hemostatic surgical system;

FIG. 4 is an exploded isometric view of the shank and blade support arms for a first embodiment of the present disclosure;

FIG. 5 is an end view of the blade support arms for a first embodiment of the present disclosure;

FIG. 6 is an isometric view of a subassembly comprising the shank and support arms for a first embodiment of the present disclosure;

FIG. 7 is a side view of a subassembly comprising the shank and support arms for a first embodiment of the present disclosure;

FIG. 8 is a top view of the thermal barrier member and its carrier provided to facilitate assembly;

FIG. 9 is an isometric view of the thermal barrier member and its carrier provided to facilitate assembly;

FIG. 10 is an enlarged top view of the thermal barrier member as referenced in Detail A of FIG. 9;

FIG. 11 is an isometric view of the handpiece, shank, blade support arms and blade for a second embodiment of the present disclosure;

FIG. 12A is an exploded isometric view of the handpiece, shank, blade support arms and blade for a second embodiment of the present disclosure;

FIG. 12B is detailed side view of second thermally conductive blade support arm;

FIG. 12C is isometric view of distal end of thermally conductive blade support shank showing first and second thermally conductive blade support arms;

FIG. 12D is top view of thermally conductive blade support shank and first and second thermally conductive blade support arms;

FIG. 12E is side view of thermally conductive blade support shank and first and second thermally conductive blade support arms;

FIG. 13 is an isometric view of the flexible circuit component incorporated in a second embodiment of the present disclosure;

FIG. 14 is an isometric view of a surgically sharp blade with straight cutting edge;

FIG. 15 is a top view of a surgically sharp blade with straight cutting edge;

FIG. 15A is a cross-sectional view of a surgically sharp blade with straight cutting edge;

FIG. 16 is a top view of a surgically sharp blade with straight cutting edge and electrical heater disposed thereon;

FIG. 21 is a cross-sectional view of a blade comprising an electrically resistive and thermally conductive blade and non-stick coating covering entire blade except for tip of cutting edge;

FIG. 22 is a cross-sectional view of a blade comprising an electrically resistive, ferromagnetic or ferrimagnetic layer disposed on the surface of an non-ferromagnetic or non-ferrimagnetic, electrically and thermally conductive blade with an optional non-stick coating covering entire blade except for tip of cutting edge;

FIG. 23 is top view of four-conductor flexible circuit lead pattern for conducting current to contact pads and lead pattern for measuring tissue impedance;

FIG. 24 is a detailed top view of proximal end of four-conductor flexible circuit lead pattern for conducting current to contact pads and lead pattern for measuring tissue impedance;

FIG. 25 is a detailed top view of mid-length portion of four-conductor flexible circuit at location in which power leads and sense leads branch corresponding to first and second blade support arms;

FIG. 26 is a detailed top view of distal end portion of four-conductor flexible circuit at location in which electrical contact pads for power lead and sense lead are positioned corresponding to second blade support arm;

FIG. 27 is cross-section view of tissue and end view of curette assembly illustrating current flux lines in tissue used to measure electrical impedance of underlying tissue;

FIG. 28 is cross-sectional view of assembly comprising blade, blade support arm, washers, insulating sleeve, heating element, heater lead and sensor lead;

FIG. 29 is a detailed cross-sectional view of region in which power lead electrical contact pad is in electrical communication with electrical contact pad on heatable blade; and FIGS. 30A and 30B combine as labeled thereon to provide a flow chart describing the operation and use of the apparatus and system for the excision of soft tissue in humans using a mechanically sharp, heatable blade of the present disclosure as seen in FIGS. 1-29.

Figure 3:
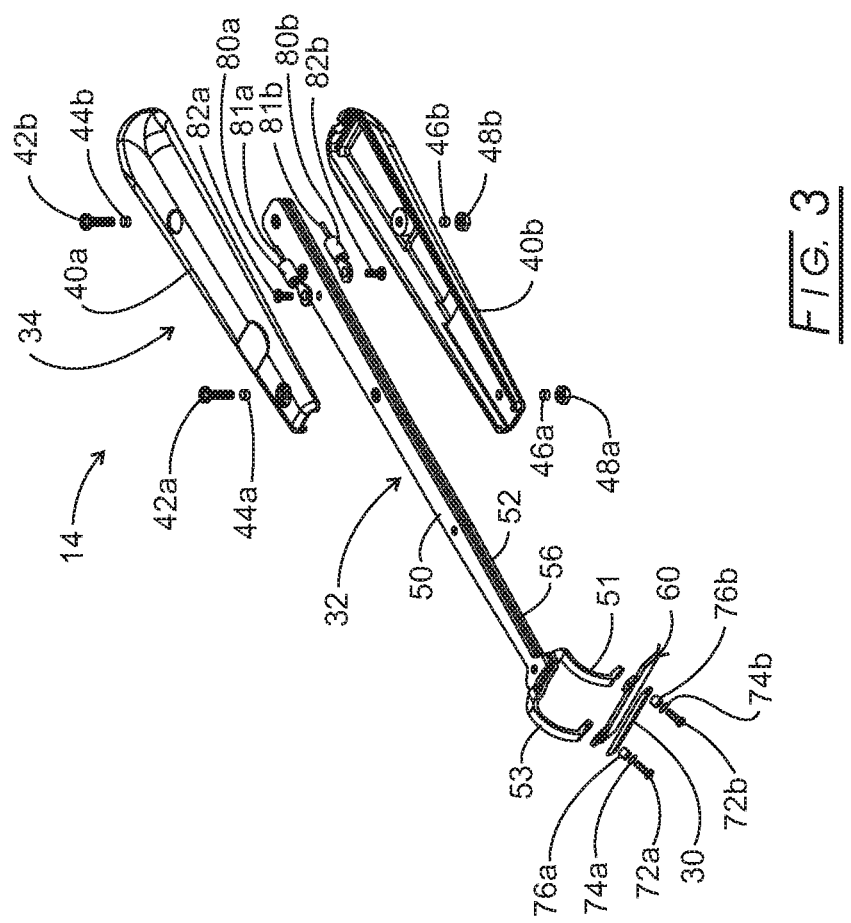
FIG. 3 is an exploded isometric view of the handpiece, shank, blade support arms and blade for a first embodiment of the present disclosure.

The drawings will be described in further detail below.

DETAILED DESCRIPTION

The present disclosure for the excision of soft tissue in humans using a mechanically sharp, heated blade is seen in the system shown in FIG. 1. As seen in FIG. 1, a system, 10, comprises a controller, 12, a handpiece, 14, connected to controller 12 via a handpiece cable, 36, a footpedal, 16, connected to controller 12 via a footpedal cable, 22. Still referring to FIG. 1, handpiece 14 comprises a handle, 34, a blade support member, 32, and a heatable blade, 30. Handpiece cable 36 extending from handpiece 14 is connected to controller 12 using a removably attachable handpiece cable connector, 38. Footpedal 16 comprises a first pedal, 18, to activate and control application of power to heatable blade 30 during tissue cutting at preselected set-point temperature, T1. Footpedal 16 also comprises a second footpedal, 20, to activate and control application of power to heatable blade 30 during optional blood vessel sealing following tissue cutting at preselected set-point temperature, T2. A footpedal cable, 22, extending from footpedal 16 is connected to controller 12 using removably an attachable footpedal cable connector, 24. As seen in FIG. 1, controller 12 includes an on/off power switch, 39, a set-point temperature decrease control switch, 41, a set-point temperature increase control switch, 43, as well as a temperature set-point and operating status as indicated on display screen, 45.

Figure 2:
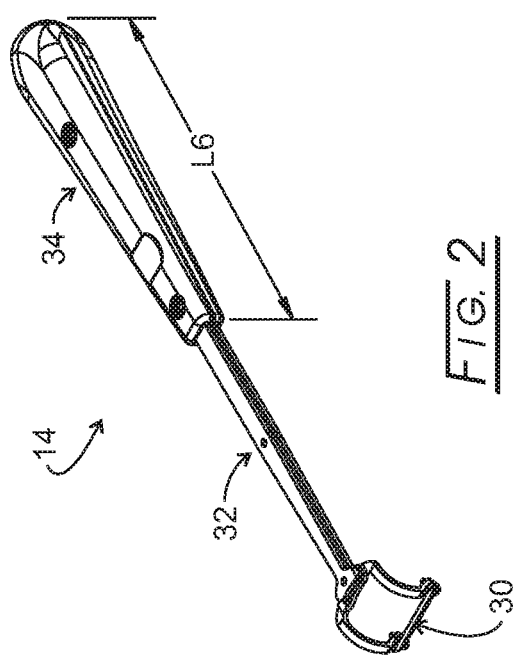
FIG. 2 is an isometric view of the handpiece, shank, blade support arms and blade for a first embodiment of the present disclosure.

Referring now to FIGS. 2 and 3, handpiece 14 is illustrated in greater detail. As seen in FIG. 2, handpiece 14 comprises a handle, 34, a blade support member, 32, and a heatable blade, 30. As seen in FIG. 3, a blade support member, 32, comprises two electrically and thermally conductive blade support shanks, 50 and 52, and two electrically and thermally conductive blade support arms, 51 and 53, respectively. Electrically and thermally conductive blade support shank 50 and integral blade support arm 51 are electrically isolated from the electrically and thermally conductive blade support shank 52 and integral blade support arm 53 by an electrically insulative spacer, 56. An exploded view of handpiece 14 is seen in FIG. 3. Handle 34 comprises first and second handle shell halves, 40a and 40b, that enclose the proximal end of blade support member 32 and mechanically attached to one another by first and second fastening screws, 42a and 42b, in combination with first and second fastening nuts, 48a and 48b, respectively. As seen in FIG. 3, the first and second fastening screws 42a and 42b are electrically isolated from blade support member 32 by first and second electrically insulative sleeve pairs, 44a, 46a and 44b, 46b.

Still referring to FIG. 3, blade support member is seen in isometric view comprising first electrically and thermally conductive blade support shank 50 and second electrically and thermally conductive blade support shank 52 surrounding an intervening electrically insulative spacer, 56, that electrically isolates the first electrically and thermally conductive blade support shank 50 from the second electrically and thermally conductive blade support shank 52. First and second electrical lead connectors, 80a and 80b, in electrical communication with first and second electrical leads, 81a and 81b, respectively, are in electrical communication with and fastened to first electrically and thermally conductive blade support shank 50 and second electrically and thermally conductive blade support shank 52, respectively, using first and second electrical lead connector fastening screws, 82a and 82b, respectively.

Still referring to FIG. 3, first electrically and thermally conductive blade support arm 51 extends from first electrically and thermally conductive blade support shank 50. In like manner, second electrically and thermally conductive blade support arm 53 extends from second electrically and thermally conductive blade support shank 52. During an assembly step, heatable blade 30 is mechanically fastened to first electrically and thermally conductive blade support arm 51 and second electrically and thermally conductive blade support arm 53 with intervening a thermal barrier assembly, 60. The mechanical fastening is accomplished with first and second fastening screws, 72a and 72b, with electrically and thermally insulative sleeves, 76a and 76b, surrounding exposed portion of fastening screws to electrically and thermally isolate the fastening screws 72a and 72b from heatable blade 30. In addition, electrically and thermally insulative washers, 74a and 74b, are positioned between fastening screws 72a and 72b and heatable blade 30 to electrically and thermally isolate the fastening screws 72a and 72b from heatable blade 30. By way of example, one-piece thermally conductive blade support arm 51 and integral thermally conductive blade support shank 50, as well as one-piece thermally conductive blade support arm 53 and integral thermally conductive blade support shank 52, are preferably a high copper content electrically and thermally conductive metal such as Oxygen Free Hard Copper (OHFC) or other materials such as, for example, high-strength aluminum alloys.

Turning now to FIG. 4, blade support member 32 is seen in an exploded isometric view comprising first electrically and thermally conductive blade support shank 50 and second electrically and thermally conductive blade support shank 52 surrounding intervening electrically insulative spacer 56. In a preferred embodiment, a first adhesive layer, 54, is positioned between first electrically and thermally conductive blade support shank 50 and intervening electrically insulative spacer 56. Likewise, a second adhesive layer, 58, is positioned between second electrically and thermally conductive blade support shank 52 and intervening electrically insulative spacer 56. In addition to adhesive bonding of a subassembly comprising first electrically and thermally conductive blade support shank 50, intervening electrically insulative spacer 56 and second electrically and thermally conductive blade support shank 52, first and second fastening screws, 84a and 84b, are used to mechanically attach and form the composite subassembly comprising first electrically and thermally conductive blade support shank 50, intervening electrically insulative spacer 56 and second electrically and thermally conductive blade support shank 52. As seen in FIG. 4, electrically insulative washers, 86a and 86b, and electrically insulative sleeves, 88a and 88b, electrically isolate fastening screws 84a and 84b, respectively, from electrically and thermally conductive blade support shank 52.

The distal end of blade support member 32 is seen in isometric view in FIG. 5 revealing [a] threaded holes 55a and 55b in distal ends of electrically and thermally conductive blade support arms 51 and 53, respectively, and [b] fastening screw 84a and electrically insulative washer 86a that mechanically fastens first electrically and thermally conductive blade support shank 50 to second electrically and thermally conductive blade support shank 52 on either surface of intervening electrically insulative spacer 56. Isometric and side views of blade support member 32 are additionally provided in FIGS. 6 and 7.

Turning now to FIGS. 8, 9 and 10, thermal barrier assembly 60, as well as first and second thermally and electrically insulative spacers, 62a and 62b, are seen in greater detail. As seen in FIG. 8, a thermal barrier assembly comprises thermal barrier member carrier, 61, as well as first and second thermally and electrically insulative spacers 62a and 62b. As seen in FIGS. 8 and 10, the first and second thermally and electrically insulative spacers 62a and 62b are surmounted by first and second electrical contact pads, 64a and 64b, and first and second electrically conductive vias, 66a and 66b, respectively. The first and second electrically conductive vias 66a and 66b provide electrical communication with corresponding first and second electrical contact pads on opposite face of electrically insulative spacers 62a and 62b (not shown). The first and second electrical contact pads 64a and 64b are electrically connected to corresponding electrical contact pads on heatable blade using high-temperature electrically conductive adhesive, by way of example but not limitation, an adhesive such as EPO-TEK H20E supplied by Epoxy Technology, Inc., Billerica, Mass. (adhesive layer not shown). Likewise, first and second electrical contact pads on opposite face of electrically insulative spacers 62a and 62b (not shown) are electrically connected to corresponding electrical contact surfaces on first electrically and thermally conductive blade support arm 51 and second electrically and thermally conductive blade support arm 53, respectively. As seen in FIG. 8, first and second scored neck regions, 63a and 63b, enable the thermal barrier member carrier 61 with attached first and second thermally insulative spacers 62a and 62b to be readily separated along the first and second score lines 63a and 63b, respectively, after the above specified electrically conductive adhesive bonding process has been completed.

By way of example but not limitation and referring to FIG. 8, EPO-TEK H20E may be screen printed on the first and second electrical contact pads 64a and 64b on the first surface of the thermally insulative spacers 62a and 62b, respectively. Next, the EPO-TEK H20E may be screen printed on the first and second electrical contact pads on the second surface of the thermally insulative spacers 62a and 62b (not shown) corresponding to and in electrical communication with first and second electrical contact pads 64a and 64b, respectively. Next and referring to FIGS. 3 and 8, the subassembly comprising the heatable blade 30 and thermal barrier assembly 60, with screen printed electrically conductive adhesive on both sides of first and second thermally insulative spacers 62a and 62b, is mechanically fastened to first and second electrically and thermally conductive blade support arms 51 and 53 using first and second fastening screws, 72a and 72b. Next the mechanically fastened subassembly is placed in an air convention oven for 15 minutes at a temperature of 120° C. to cure the adhesive and effect the electrically conductive bonds at [a] the interfaces with contact pads, 164a and 164b, surmounted on heatable blade 30 (as seen in FIG. 16) and the interfaces with the first and second electrically and thermally conductive blade support arms 51 and 53. Finally, referring to FIGS. 2 and 8, the thermal barrier member carrier 61 is separated from the first and second thermally insulative spacers 62a and 62b to provide a subassembly comprising [a] electrically conductive bonds between first and second electrical contact pads 64a and 64b and contact pads 164a and 164b surmounted on heatable blade 30 as well as [b] electrically conductive bonds between first and second electrical contact pads on the second surface of the thermally insulative spacers 62a and 62b (not shown) and electrically conductive surface of electrically and thermally conductive blade support arms 51 and 53, respectively, as seen in FIG. 2.

As seen in FIGS. 2 through 7, the first embodiment of the present disclosure enables the conduction of heating current from leads 81a and 81b to the heatable blade 30 via first and second electrically and thermally conductive blade support shanks 50 and 52 and extending to the tip of first and second electrically and thermally conductive blade support arms 51 and 53, respectively. As seen in FIG. 4, electrically insulative spacer 56 assures electrical isolation between first and second electrically and thermally conductive blade support shanks 50 and 52. Still referring to FIG. 4, adhesive bonds between first and second electrically and thermally conductive blade support shanks 50 and 52 and interspaced electrically insulative spacer 56 is provided by first and second double-sided adhesive layers 54 and 58. The adhesive bonds results in a multi-layer cantilever beam sandwich with improved stiffness to reduce deflection in the presence of applied forces at the distal end of blade support member 32 associated with tissue excision, tamponade, and sealing of transected blood vessels.

The exposed heads of first and second fastening screws 72a and 72b are coated with an electrically insulative and biocompatible coating to prevent electrical stimulation of in vivo tissue, if electrical heating current frequency supplied to heatable blade 30 is less than about 50 kHz. By way of example but without limitation, the electrically insulative and biocompatible coating may be an applied coating of Parylene C having a thickness in the range from 0.0003 to 0.0020 inch having a thickness in the range from 0.0003 to 0.0020 inch (Specialty Coating Systems, Inc., Indianapolis, Ind.). Also, the exposed surfaces of electrically and thermally conductive blade support shank 50 and integral blade support arm 51, as well as electrically and thermally conductive blade support shank 52 and integral blade support arm 53, are coated with an electrically insulative and biocompatible coating. By way of example but without limitation, the electrically insulative and biocompatible coating may be an applied coating of Parylene C having a thickness in the range from 0.0003 to 0.0020 inch (Specialty Coating Systems, Inc., Indianapolis, Ind.).

In the design of the first embodiment of the present disclosure, as seen in FIGS. 2 through 7, [a] the widths and thicknesses of electrically and thermally conductive blade support shanks 50 and 52 and first and second electrically and thermally conductive blade support arms 51 and 53, [b] the width and thickness of thermally insulative spacers 62a and 62b, [c] the metal or alloy selected for use in the construction of thermally conductive blade support shanks 50 and 52 and integral thermally conductive blade support arms 51 and 53, [d] the material selected for use in the construction of thermally insulative spacers 62a and 62b, [e] the thickness and material selected for first and second electrically and thermally insulative washers 74a and 74b, [f] the thickness and material selected for first and second electrically and thermally insulative sleeves 76a and 76b and [g] the diameter and material selected for first and second fastening screws 72a and 72b have all been selected to reduce the conduction of heat from the heated blade 30 (e.g., operating at a temperature in the range from about 150° to 250° C. during tissue excision and sealing of blood vessels) to the first and second electrically and thermally conductive blade support arms 51 and 53 so that the maximum temperature of the exposed surfaces of the electrically and thermally conductive blade support arms 51 and 53 do not exceed about 50° C. during an excision and coagulation procedure. By maintaining the maximum temperature of the exposed surfaces of the electrically and thermally conductive blade support arms 51 and 53 at or below about 50° C. during the expected exposure duration associated with an excision and coagulation procedure, unwanted thermal injury to surrounding healthy tissue is avoided. The preferred dimensions of thermally conductive blade support shanks 50 and 52 and integral thermally conductive blade support arms 51 and 53, as well as the thermally insulative spacers 62a and 62b, electrically and thermally insulative washers 74a and 74b, and electrically and thermally insulative sleeves 76a and 76b are provided in a subsequent section of this specification and associated referenced drawings.

By way of example and referring to FIGS. 2 through 7, electrically and thermally conductive blade support shanks 50 and 52 and integral electrically and thermally conductive blade support arms 51 and 53 may be Oxygen Free Hard Copper or selected from other high-copper content copper alloys or selected from high-aluminum content aluminum alloys providing a thermal conductivity of at least 1.5 watts/cm-C. Elongated electrically and thermally conductive blade support shanks 50 and 52 may be malleable to enable an operator to manually alter the shape of elongated blade support shanks 50 and 52 to improve access to an intended surgical site. Thermally insulative spacers 62a and 62b may advantageously be constructed using polyimide material, such as Polyimide Laminate 85N (e.g., available from Arlon Technologies, Rancho Cucamonga, Calif.). Electrically and thermally insulative washers 74a and 74b may advantageously be constructed using polyimide material, such as Kapton (e.g., available from Boker's Inc., Minneapolis, Minn.). Electrically and thermally insulative sleeves 76a and 76b may advantageously be constructed using polyimide material (e.g., available from MicroLumen, Inc., Oldsmar, Fla.). Fastening screws 72a and 72b (e.g., screw size 80 or 90) may advantageously be constructed using stainless steel Type 304 or Type 316 (e.g., available from US Microscrew, Seattle, Wash.).

A second embodiment of the present disclosure is illustrated in FIGS. 11 through 13. Unlike the first embodiment of the present disclosure as seen in FIGS. 2 through 7 and described in the preceding paragraphs, the conduction of heating current, as seen in FIGS. 11 through 13, from leads 116a and 116b to heatable blade 30 is accomplished via first and second electrically conductive leads, 152 and 154, disposed on an electrically insulative flexible substrate, 150, and extending to the tip of first and second thermally conductive blade support arms 131a and 131b.

In the design of the second embodiment of the present disclosure, as seen in FIGS. 11 through 13, [a] the widths and thicknesses of thermally conductive blade support shanks, 104, and first and second electrically and thermally conductive blade support arms, 131a and 131b, [b] the width and thickness of the thermally insulative spacers 62a and 62b, [c] the metal or alloy selected for use in the construction of thermally conductive blade support shank 104 and integral thermally conductive blade support arms 131a and 131b, [d] the material selected for use in construction of the thermally insulative spacers 62a and 62b, [e] the thickness and material selected for first and second electrically and thermally insulative washers 144a and 144b, [f] the thickness and material selected for first and second electrically and thermally insulative sleeves 146a and 146b and [g] the diameter and material selected for first and second fastening screws 142a and 142b have all been selected to reduce the conduction of heat from the heated blade 30 (e.g., operating at a temperature of 150° to 250° C. during tissue excision and sealing of blood vessels) to first and second electrically and thermally conductive blade support arms 131a and 131b, so that the maximum temperature of the exposed surfaces of electrically and thermally conductive blade support arms 131a and 131b do not exceed about 50° C. during an excision and coagulation procedure. By maintaining the maximum temperature of the exposed surfaces of electrically and thermally conductive blade support arms 131a and 131b at or below about 50° C. during an excision and coagulation procedure, unwanted thermal injury to surrounding healthy tissue is avoided. The preferred dimensions of thermally conductive blade support shank 104 and integral thermally conductive blade support arms 131a and 131b, as well as the thermally insulative spacers 62a, 62b, electrically and thermally insulative washers 144a, 144b, electrically and thermally insulative sleeves 146a, 146b, and fastening screws 142a, 142b are provided in a subsequent section of this description and associated referenced drawings. The holes for screws 142a and 142b are indicated as items 159a and 159b, respectively in FIG. 13.

By way of example and referring to FIGS. 11 through 13, thermally conductive blade support shank 104 and integral thermally conductive blade support arms 131a and 131b may be Oxygen Free Hard Copper or selected from other high-copper content copper alloys or selected from high-aluminum content aluminum alloys providing a thermal conductivity of at least 1.5 watts/cm-C. Thermally insulative spacers 62a and 62b may advantageously be constructed using polyimide material, such as Polyimide Laminate 85N (e.g., available from Arlon Technologies, Rancho Cucamonga, Calif.). Electrically and thermally insulative washers 144a and 144b may advantageously be constructed using polyimide material, such as Kapton (e.g., available from Boker's Inc., Minneapolis, Minn.). Electrically and thermally insulative sleeves 146a and 146b may advantageously be constructed using polyimide material (e.g., available from MicroLumen, Inc., Oldsmar, Fla.). Fastening screws 142a and 142b may advantageously be constructed using stainless steel Type 304 or Type 315 (e.g., available from US Microscrew, Seattle, Wash.). The exposed surfaces of thermally conductive blade support shank 104 and integral blade support arms 131a and 131b are coated with a biocompatible coating. By way of example but without limitation, the biocompatible coating may be an applied coating of Parylene C having a thickness in the range from 0.0003 to 0.0020 inch (Specialty Coating Systems, Inc., Indianapolis, Ind.).

As seen in FIG. 11, a handpiece comprises handle, 100, thermally conductive blade support member, 110, first and second thermally conductive blade support arms 131a and 131b and heatable blade 30. Referring now to FIGS. 11 and 12A, handpiece 14 is shown in greater detail. As seen in the exploded isometric view in FIG. 12A, handle 100 comprises first and second handle shell halves 102a and 102b that enclose the proximal end of blade support member 110 and are mechanically attached to one another by first and second fastening screws 112a and 112b in combination with first and second fastening nuts 114a and 114b, respectively, with spacer plate 108 positioned against the second surface of thermally conductive blade support shank. Still referring to FIG. 12A, blade support member 110 comprises thermally conductive blade support shank 104 that extends distally to first and second thermally conductive blade support arms 131a and 131b.

Referring now to FIGS. 12A and 13, a two-conductor flexible circuit, 106, is surmounted on and adhesively attached (e.g., using pressure sensitive adhesive such as 3M Cat. No. 9082 manufactured by 3M Company, Minneapolis, Minn.) to thermally conductive blade support shank 104 providing electrical communication between [a] first and second electrical connectors 116a and 116b positioned at proximal end of two-conductor flexible circuit 106 and [b] first and second electrical contact pads 158a and 158b positioned at distal end of two-conductor flexible circuit 106 via first and second electrically conducting lead 152 and 154, respectively. By way of example and without limitation and referring to FIG. 13, two-conductor flexible circuit 106 may be fabricated by adhesively bonding thin copper foil, having a thickness in the range from 0.0007 inch to 0.0028 inch, to flexible electrically insulative polyimide substrate 150, such as Kapton (DuPont, Wilmington, Del.) having a thickness in the range from 0.001 inch to 0.004 inch. Photolithography is then used to selectively chemically etch and remove certain portions of the adhesively bonded copper on a flexible polyimide substrate to provide a preferred electrically conductive lead pattern. As seen in FIG. 13, photolithography and selective chemical etching is used to produce two-conductor flexible circuit 106 comprising [a] first electrically conductive lead trace 152 disposed on electrically insulative flexible polyimide substrate 150 that extends from proximal end of two-conductor flexible circuit 106 to [a] a first branching arm lead trace, 153, and first electrical contact pad 158a and [b] second electrically conductive lead trace 154 disposed on electrically insulative flexible polyimide substrate 150 that extends to a second branching arm lead trace, 155, and second electrical contact pad 158b.

Returning to exploded view of handpiece 14 in FIG. 12A, first and second electrical lead connectors 116a and 116b in electrical communication with first and second electrical leads 115a and 115b, respectively, are in placed in electrical communication with the proximal ends of first and second electrically conducting leads 152 and 154, respectively. First and second electrical lead connectors 116a and 116b are fastened to and electrically insulated from thermally conductive blade support shank 104 using first and second electrical lead connector fastening screws 118a and 118b, respectively, in combination with first and second electrically insulative sleeves, 117a, 117b, and first and second fastening nuts, 119a, 119b, respectively.

Still referring to FIG. 12A, spacer plate 108 is positioned between blade support member 104 and second handle shell half 102b to provide increased stability of blade support member 104 in the presence of applied forces at the distal end of blade support member 104 at first and second thermally conductive blade support arms 131a, 131b and supported heatable blade 30, the applied forces associated with tissue excision, tamponade and sealing of transected blood vessels.

By way of example and without limitation, still referring to FIG. 12A, first and second thermally conductive blade support arms 131a and 131b extend from thermally conductive blade support shank 104. During an assembly step, heatable blade 30 is mechanically fastened to first and second thermally conductive blade support arms 131a and 131b with an intervening thermal barrier assembly, 130. The mechanical fastening is accomplished with first and second fastening screws 142a and 142b with electrically and thermally insulative sleeves 146a and 146b surrounding exposed portion of fastening screws to electrically and thermally isolate the fastening screws 142a and 142b from heatable blade 30. In addition, electrically and thermally insulative washers 144a and 144b are positioned between fastening screws 142a and 142b and heatable blade 30 to electrically and thermally isolate the fastening screws 142a and 142b from heatable blade 30. Referring now to FIGS. 12A, 13, and 16, the mechanical assembly with electrically conductive adhesive applied between first and second electrical contact pads 158a, 158b at the distal end of two-conductor flexible circuit 106 and corresponding first and second blade heater electrical contact pads 164a, 164b is next placed in a convection oven (e.g., at 120° C. for 15 minutes) to cure the electrically conductive adhesive. The first and second electrical contact pads 158a and 158b are electrically connected to corresponding first and second electrical contact pads 164a and 164b on heatable blade using high-temperature electrically conductive adhesive, by way of example but not limitation, an adhesive such as EPO-TEK H20E that cures at 120° C. for a 15 minute heating period (adhesive layer not shown). The EPO-TEK H20E adhesive is supplied by Epoxy Technology, Inc., Billerica, Mass.

Referring next to FIGS. 12B through 12E, alternative views of thermally conductive blade support member 104 and integral first and second thermally conductive blade support arms 131a and 131b are provided with dimensional annotations that refer to the range of preferred dimensions indicated in a subsequent section of this specification.

Turning now to FIGS. 14 through 16, alternative views of heatable blade 30, as incorporated in the first and second embodiments of the tissue excision system of the present disclosure, are provided including an isometric view of a first surface, 185, of heatable blade 30 (as seen in FIG. 14), top view of first surface 185 of heatable blade 30 (as seen in FIG. 15), cross-sectional view of heatable blade 30 (as seen in FIG. 15A) and top view of a planar second surface, 187, of heatable blade 30 surmounted by an electrically insulative layer, 160, an electrically conductive heating element, 162, first and second blade heater contact pads, 164a, 164b, (as seen in FIG. 16). As seen in FIGS. 14, 15 and 15A, heatable blade 30 comprises first surface 185 of a thermally conductive blade substrate, 170, including a single-bevel region, 180, with included angle φ1, a flat region, 186, first and second through holes, 182a, 182b. As seen in FIGS. 15A and 16, heatable blade 30 comprises a planar second surface, 187, of thermally conductive blade substrate 170. As seen in FIGS. 14, 15 and 16, heatable blade 30 is configured with a straight cutting edge, 189. As seen in FIGS. 14, 15 and 16, indexing notches, 184a and 184b, may be included on perimeter of thermally conductive blade substrate 170 opposite cutting edge 189 to facilitate registration of thermally conductive blade substrate 170 during thick film printing process.

Figure 17:
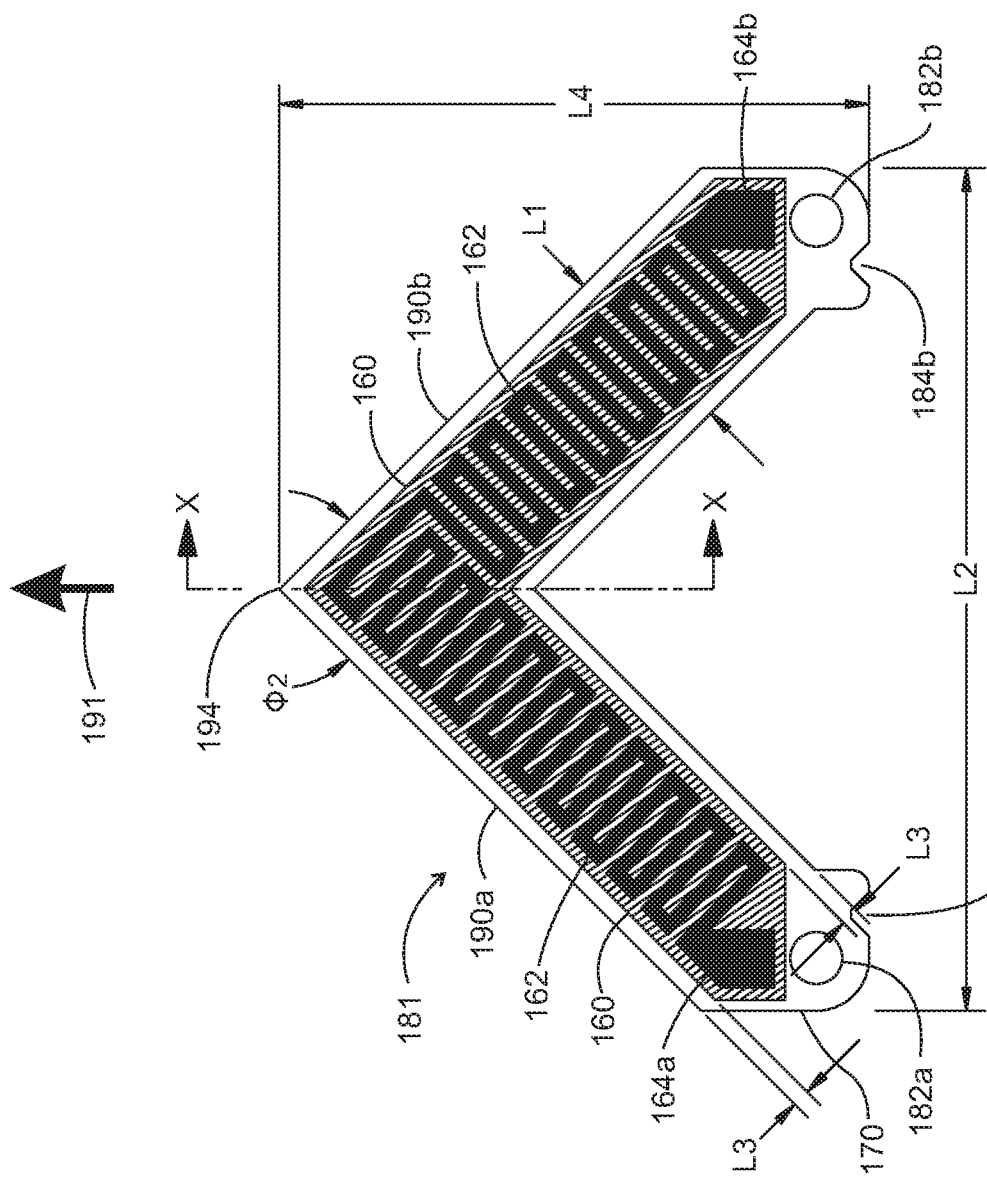
FIG. 17 is a top view of a surgically sharp blade with triangular cutting edge and electrical heater disposed thereon.
Figure 18:
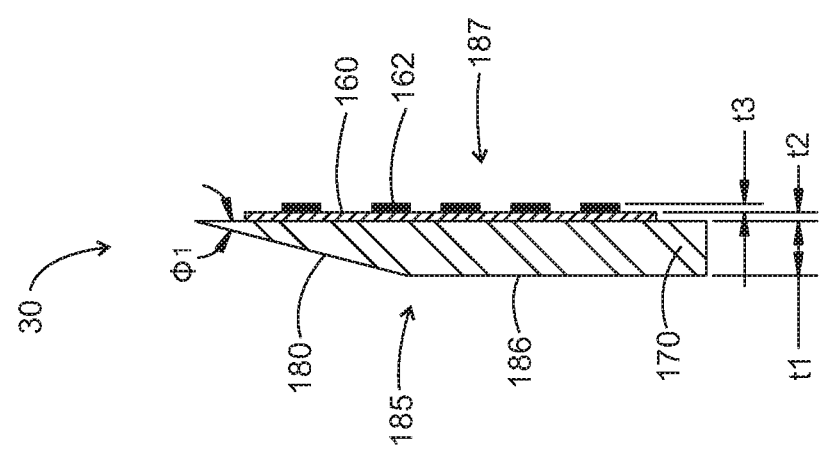
FIG. 18 is a cross-sectional view of a surgically sharp blade with triangular cutting edge and electrical heater disposed thereon as referenced in FIG. 17 as Section X-X.

Turning now to FIGS. 17 and 18, an alternative embodiment of heatable blade 30 is seen wherein the heatable blade 30 is configured with a triangular shaped blade, 181, having cutting edges, 190a, 190b, disposed on either side of a triangular blade apex, 194. As incorporated in the first and second embodiments of the tissue excision system of the present disclosure, alternative embodiment of heatable blade 30, as seen in FIG. 17, includes top view of a planar second surface, 187, of heatable blade 30 surmounted by electrically insulative layer 160, electrically conductive heating element 162, first and second blade heater contact pads 164a, 164b. A cross-sectional view of alternative embodiment of heatable blade 30 is seen in FIG. 18 comprising first surface 185 of thermally conductive blade substrate 170 including single-bevel region 180 with included angle φ1, flat region 186, first and second through holes 182a, 182b, and planar second surface 187 surmounted by electrically insulative layer 160 and electrically conductive heating element 162. Returning to FIG. 17, heatable blade 30 is configured as a triangular shaped cutting edge, 190, with included angle, φ2 to reduce the force required for the incision of tissue due to the angle of the cutting edges, 190a, 190b, relative to cutting direction, 191.

Figure 19:
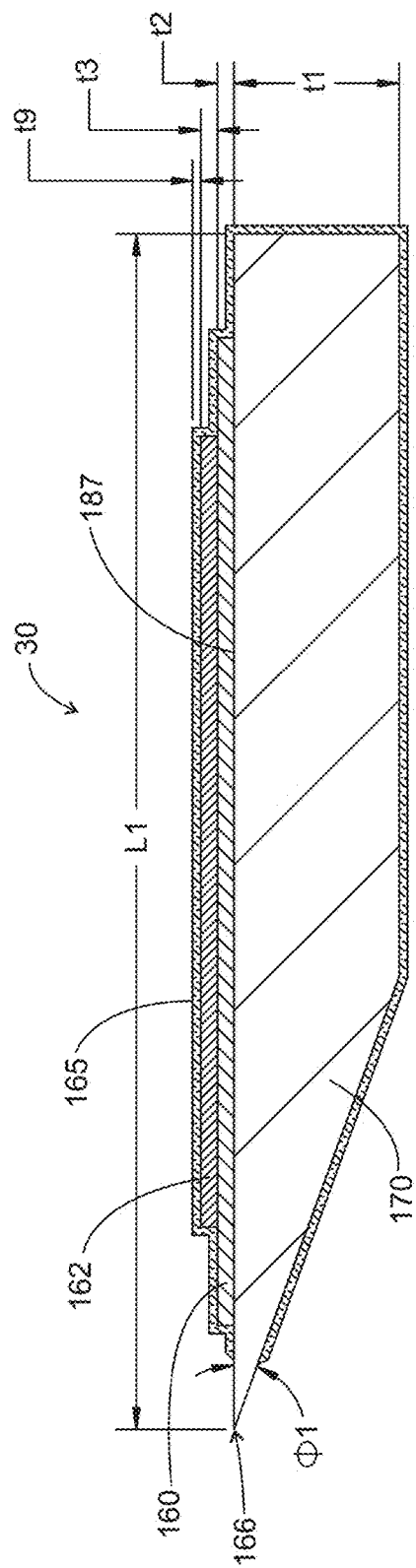
FIG. 19 is a cross-sectional view of a blade comprising an electrically and thermally conductive blade, electrically insulative layer disposed on blade, electrically resistive heater disposed on the electrically insulative layer and non-stick coating covering entire blade except for tip of cutting edge.

Turning now to FIGS. 19 through 22, several different embodiments are specified for the electrical heating of heatable blade 30, as incorporated in the first and second embodiments of the tissue excision system of the present disclosure. In the cross-section view of heatable blade 30 seen in FIG. 19, second surface 187 of thermally conductive blade substrate 170 is surmounted first by electrically insulative layer 160 and then electrically conductive heating element 162 is disposed on the electrically insulative layer 160. The exterior surface of heatable blade 30 is covered with a non-stick coating, 165, except at a cutting edge tip region, 166, preferably exposing an uncoated length of cutting edge tip region 166 ranging from 0.003 to 0.010 inch. Non-stick coating 165 minimizes adherence of tissue and coagulum during tissue incision. In addition, non-stick coating 165, if selected with electrically insulative characteristics, to electrically isolate heating element 162 from tissue contacted during tissue incision. Alternatively, prior to the application of non-stick coating 165, a second electrically insulative layer (not shown) may be disposed over layer of heating element 162 using the same electrically insulative material as used for electrically insulative layer 160 to electrically isolate heating element 162 from tissue contacted during tissue incision. The heating current induced within heating element 162 may range from direct current to alternating current having a frequency of up to about one megahertz, preferably in the range from at least 100 to 400 kilohertz to minimize the effects of nerve stimulation. The temperature of the blade is preferably controlled by heater resistance feedback control enabled by the high temperature coefficient of resistance (TCR) of the conductive material incorporated into the glass matrix of the electrically conductive heating element 162 as described in U.S. Pat. No. 8,475,444, incorporated herein by reference. By way of example and without limitation, [a] thermally conductive blade substrate 170 may be GIN-5 martensitic stainless steel heat treated to a hardness of at least 58 Rockwell C (Hitachi Metals America, Ltd., Arlington Heights, Ill.), [b] electrically insulative layer 160 may be a screen-printable glass dielectric layer (ElectroScience Laboratories, King of Prussia, Pa.) and electrically conductive heating element 162 may be a silver-filled, screen-printable glass layer (ElectroScience Laboratories, King of Prussia, Pa.). Non-stick coating 165 may be a polytetrafluoroethylene coating (Whitford Corporation, Elverson, Pa.). Other dimensions of the blade and disposed layers comprising heatable blade 30, as seen in FIG. 19, are designated as noted and are specified below.

Figure 20:
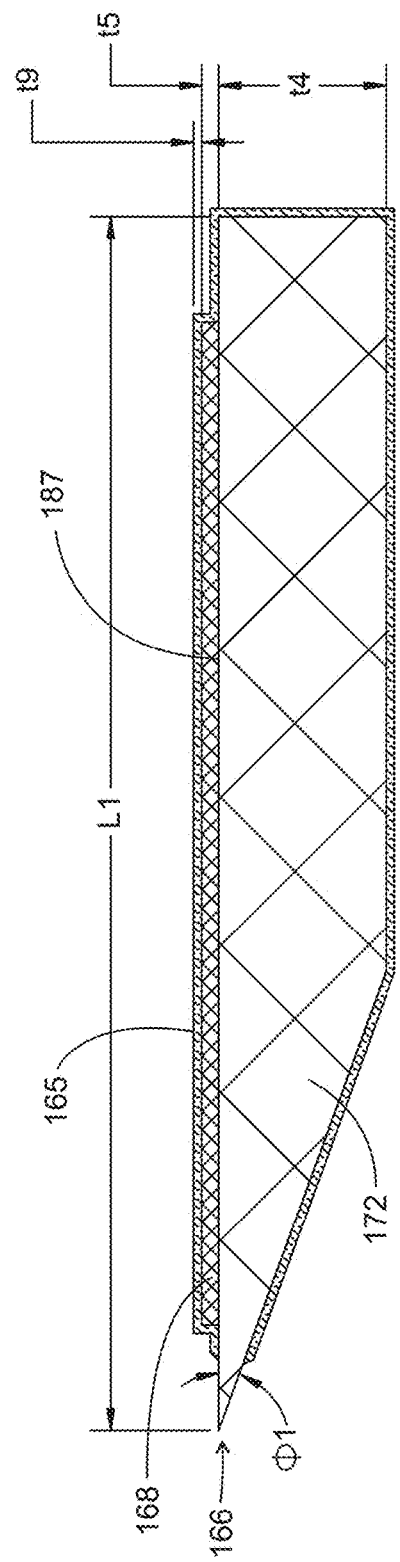
FIG. 20 is a cross-sectional view of a blade comprising an electrically insulative and thermally conductive blade, electrically resistive heater disposed on the electrically insulative and thermally conductive blade and non-stick coating covering entire blade except for tip of cutting edge.

In the cross-section view of heatable blade 30 seen in FIG. 20, second surface 187 of electrically insulative and thermally conductive blade substrate 172 is surmounted by an electrically conductive heating element, 168, disposed on surface of the electrically insulative and thermally conductive blade substrate 172. The exterior surface of heatable blade 30 is covered with non-stick coating 165 except at the cutting edge tip region 166, preferably exposing an uncoated length of the cutting edge tip region 166 ranging from 0.003 to 0.010 inch. Non-stick coating 165 minimizes adherence of tissue and coagulum during tissue incision. In addition, non-stick coating 165, if selected with electrically insulative characteristics, to electrically isolate heating element 162 from tissue contacted during tissue incision. Alternatively, prior to the application of non-stick coating 165, an electrically insulative layer (not shown) may be disposed over layer of heating element 162 using the same electrically insulative material as used for electrically insulative layer 160 (as seen in FIG. 19) to electrically isolate heating element 162 from tissue contacted during tissue incision. The heating current induced within heating element 168 may range from direct current to alternating current having a frequency of up to about one megahertz, preferably in the range from at least 100 to 400 kilohertz to minimize the effects of nerve stimulation. The temperature of the blade is preferably controlled by heater resistance feedback control enabled by the high temperature coefficient of resistance (TCR) of the conductive material incorporated into the electrically conductive heating element 162 wherein the temperature coefficient of resistance is at least 400 parts-per-million (ppm) per degree C. By way of example, electrically conductive heating element 162 may be a glass matrix of a high temperature coefficient of resistance (TCR) conductor as described in U.S. Pat. No. 8,475,444 and incorporated herein by reference. By way of example and without limitation, [a] electrically insulative and thermally conductive blade substrate 172 may be Aluminum Nitride (Ceradyne, Inc., Costa Mesa, Calif.) and electrically conductive heating element 168 may be a silver-filled, screen-printable glass layer (ElectroScience Laboratories, King of Prussia, Pa.). Non-stick coating 165 may be a polytetrafluoroethylene coating (Whitford Corporation, Elverson, Pa.). Other dimensions of the blade and disposed layers comprising heatable blade 30, as seen in FIG. 20, are designated as noted and are specified below.

In the cross-section view of heatable blade 30 seen in FIG. 21, electrically resistive and thermally conductive blade substrate 174 functions as both the cutting edge and the electrical heater. In this embodiment, referring momentarily to FIG. 15 as well as referring to FIG. 21, electrical current flows through the length, L2 of heatable blade. The exterior surface of heatable blade 30 is covered with non-stick coating 165 except at the cutting edge tip region 166, preferably exposing an uncoated length of the cutting edge tip region 166 ranging from 0.003 to 0.010 inch. The heating current induced within heating element 168 may range from direct current to alternating current having a frequency of up to about one megahertz, preferably in the range from at least 100 to 400 kilohertz to minimize the effects of nerve stimulation. The temperature of the blade is preferably controlled by temperature feedback control (temperature sensor not shown). By way of example and without limitation, electrically resistive and thermally conductive blade substrate may be silicon carbide. In this alternative embodiment, a temperature sensor is positioned in thermal communication with heatable blade 30 to measure, regulate and maintain the temperature of heatable blade 30 within a narrow range around a pre-selected set-point temperature. By way of example and without limitation, a Chromel-Alumel thermocouple may be attached to heatable blade 30 using high-temperature, thermally conductive adhesive (e.g., EPO-TEK H20E supplied by Epoxy Technology, Inc., Billerica, Mass.) to enable temperature feedback control to maintain the temperature of heatable blade 30 at 250° C.±10° C. during the intended tissue incision and optional post-incision application of heat to effect further hemostasis within transected blood vessels. Other dimensions of the blade and disposed layers comprising heatable blade 30, as seen in FIG. 21, are designated as noted and are specified below.

In the cross-section view of heatable blade 30 seen in FIG. 22, the perimeter of electrically and thermally conductive, non-ferromagnetic or non-ferrimagnetic blade substrate, 176, is coated with a ferromagnetic or ferrimagnetic material, 178. Alternatively, ferromagnetic or ferrimagnetic material 178 may extend around the entire perimeter of electrically and thermally conductive, non-ferromagnetic or non-ferrimagnetic blade substrate 176 except at the cutting edge tip region 166, preferably exposing an uncoated length of the cutting edge tip region 166 ranging from 0.003 to 0.010 inch. Following the coating of the perimeter of electrically and thermally conductive, non-ferromagnetic or non-ferrimagnetic blade substrate 176 with the ferromagnetic or ferrimagnetic material 178, the exterior surface of heatable blade 30 may be covered with non-stick coating 165 for blade operating temperatures less than about 400° C. except at cutting edge tip region 166, preferably exposing an uncoated length of cutting edge tip region 166 ranging from 0.003 to 0.010 inch. For ferromagnetic or ferrimagnetic or ferrite materials selected to operate at a blade temperature of greater than about 400° C., preferably greater than 450° C., a non stick coating is not necessary since tissue and blood coagulum adherence does not occur at blade surface temperatures above 400° C. By way of example, the coating of ferromagnetic or ferrimagnetic material 178 may be applied using vapor deposition, sputtering deposition, thermal plasma spraying, or plating process. By way of example and without limitation, thermally conductive, non-ferromagnetic or non-ferrimagnetic blade substrate 176 may be GIN-5 martensitic stainless steel heat treated to a hardness of at least 58 Rockwell C (Hitachi Metals America, Ltd., Arlington Heights, Ill.). Ferromagnetic or ferrimagnetic coating 178 may be formed from [a] an alloy containing iron and nickel, by way of example but without limitation, Permalloy (ESPI Metals, Ashland, Oreg.) and Moly Permalloy (Hamilton Precision Metals, Lancaster, Pa.) or [b] other ferromagnetic or ferrimagnetic coatings containing at least one of the following constituents: Co, Fe, Ni, $FeOFe_2O_3$, $NiOFe_2O_3$, $CuO\ Fe_2O_3$, $MgOFe_2O_3$, MnBi, MnSb, $MnOFe_2O_3$, Y3Fe5012, Gd, EuO, magnetite, yttrium iron garnet, manganese, and aluminum. Non-stick coating 165 may be a polytetrafluoroethylene coating (Whitford Corporation, Elverson, Pa.). Other dimensions of the blade and disposed layers comprising heatable blade 30, as seen in FIG. 20, are designated as noted and are specified below. The Curie temperature of ferromagnetic or ferrimagnetic coating 178 may advantageously be selected to correspond to the pre-selected temperature of heatable blade 30 during tissue incision (by way of example, a Curie temperature in the range from 150° to 600° C.). Regulation of the temperature of heatable blade 30 is achieved by the fact that current flow is no longer confined to the layer comprising ferromagnetic or ferrimagnetic coating 178, thereby effecting Curie temperature autoregulation of the temperature of heatable blade 30. In regard Curie temperature autoregulation of heating elements, refer to U.S. Pat. No. 4,256,945, which is incorporated herein by reference. Other dimensions of the blade and disposed layers comprising heatable blade 30, as seen in FIG. 22, are designated as noted and are specified below. The heating current induced within ferromagnetic or ferrimagnetic coating 178 is commonly a constant (average) electrical current level whose frequency ranges from about 4 megahertz to 24 gigahertz to induce skin effect heating wherein the current flow is predominantly confined to the surface or "skin" layer of a conductor.

Still referring to FIG. 22, ferromagnetic or ferrimagnetic coating 178 may be selected so that heatable blade 30 is maintained at a pre-selected elevated temperature (e.g., 150° C. to 30°0 C.) that is below the Curie temperature of ferromagnetic or ferrimagnetic coating 178. In this alternative embodiment, a temperature sensor is positioned in thermal communication with heatable blade 30 to measure, regulate, and maintain the temperature of heatable blade 30 within a narrow range around a pre-selected set-point temperature. By way of example and without limitation, a Chromel-Alumel thermocouple may be attached to heatable blade 30 using high-temperature, thermally conductive adhesive (e.g., EPO-TEK H20E supplied by Epoxy Technology, Inc., Billerica, Mass.) to enable temperature feedback control to maintain the temperature of heatable blade 30 at 250° C.±10° C. during the intended tissue incision and optional post-incision application of heat to effect further hemostasis within transected blood vessels. The heating current induced within ferromagnetic or ferrimagnetic coating 178 is a variable electrical current level to effect temperature feedback control. In this embodiment, the frequency ranges from about 4 megahertz to 24 gigahertz to induce skin-effect heating wherein the current flow is predominantly confined to the surface or "skin" layer represented by ferromagnetic or ferrimagnetic coating 178 in FIG. 22.

A third embodiment of the present disclosure, as seen in FIGS. 23 through 29, for the excision of tissue with a mechanically sharp, heatable blade 30 is similar to the second embodiment of the present disclosure as seen in FIGS. 11 through 13 except that a four-conductor flexible circuit, 230, replaces the two-conductor flexible circuit 106 seen in FIG. 13. Four-conductor flexible circuit 230 comprises, first and second power leads, 196a and 196b, as well as first and second sense leads, 198a and 198b (as seen in FIGS. 23, 24 and 25), that extend from first and second contact pads, 209a and 209b, respectively (as seen in FIG. 24), to first and second contact rings, 202a and 202b, respectively (as seen in FIG. 26), located at the distal end of support arms 131a and 131b, respectively (as seen in FIG. 27). Sense leads 198a, 198b (as seen in FIGS. 24 and 25) enable the application of an applied voltage between the exposed surfaces of first and second electrically conductive fastening screws 238a, 238b (as seen in FIG. 27) to determine the electrical impedance of soft tissue, 224, overlying osseous layer, 226, based on the magnitude of the measured electrical current flow between the first and second electrically conductive fastening screws 238a, 238b, as represented by current flux lines, 228 (as seen in FIG. 27).

Returning to FIG. 23, a top-view of the four-conductor flexible circuit 230 is seen with three regions designated Detail A, B, and C shown in greater detail in FIGS. 24, 25 and 26, respectively. Turning now to FIG. 24, the proximal end of the four-conductor flexible circuit 230 and designated as Detail A comprises first and second power leads 196a and 196b terminating at first and second power lead contact pads, 207a and 207b, respectively, incorporating first and second through holes, 206a and 206b, respectively, to accommodate passage of first and second power lead fastening screws (not shown), respectively. Still referring to FIG. 24, the proximal end of the four-conductor flexible circuit 230 and designated as Detail A also comprises first and second sense leads 198a and 198b terminating at first and second sense lead contact pads, 209a and 209b, respectively, incorporating first and second through holes, 208a and 208b, respectively, to accommodate passage of first and second power lead fastening screws (not shown), respectively.

Turning now to FIG. 25, the forward end of four-conductor flexible circuit 230 and designated Detail B comprises [a] first and second power leads 196a and 196b, [b] first and second sense leads 198a and 198b extending to [c] first and second braches of four-conductor flexible circuit, 236a and 236b, respectively. As seen in Detail C presented in FIG. 26, the second arm of distal end of four-conductor flexible circuit 230 corresponding to second thermally conductive support arm 131b comprises a second through hole, 193b, and a fourth through hole, 204b, at distal end of a second electrically insulative flexible extension tab substrate, 210b.

Turning now to FIGS. 27 and 28, the electrical communication between [a] the first and second power leads 196a, 196b and the heatable blade 30 and [b] the first and second sense leads 198a, 198b and the first and second electrically conductive fastening screws, 238a, 238b, is shown in greater detail. As seen in FIG. 27, an end view of blade support member 110 comprises first and second thermally conductive support arms 131a and 131b (also seen in FIGS. 12B through 12E), heatable blade 30, first and second electrically and thermally insulative spacers 62a and 62b, first and second electrically conductive fastening screws 238a and 238b, first and second thermally and electrically insulative washers 144a and 144b, first and second electrically insulative washers 214a and 214b and first and second mechanical fastening nuts 220a and 220b threaded onto first and second electrically conductive fastening screws 238a and 238b.

Referring now to FIGS. 26 and 27, first and second electrically insulative flexible extension tab substrates 210a and 210b are seen to extend from [a] distal end of four-conductor flexible circuit 230 emerging at interface between heatable blade 30 and the second electrically and thermally insulative spacers 62a and 62b to [b] interface between first and second electrically insulative washers 214a and 214b and first and second mechanical fastening nuts 220a and 220b. The first and second electrically insulative flexible extension tab substrates 210a and 210b enable first and second contact rings 202a and 202b located at distal end of first and second sense leads 198a and 198b (as seen in FIG. 26) to be in electrical communication with first and second electrically conductive fastening screws 238a and 238b. The heads of the first and second electrically conductive fastening screws 238a and 238b enable electrical communication with soft tissue 224 through direct electrical contact with soft tissue 224 as seen in FIG. 27, thereby enabling the measurement of electrical impedance of soft tissue 224 located between first and second electrically conductive fastening screws 238a and 238b. The higher the level of measured electrical impedance of soft tissue 224 located between first and second electrically conductive fastening screws 238a and 238b, the greater degree of desiccation of soft tissue 224 and the correspondingly greater degree of hemostasis within transected blood vessels.

By way of example and without limitation, a detailed cross-sectional view of distal end of first thermally conductive blade support arm 131a is seen in FIGS. 28 and 29 comprising, in sequence, first electrically conductive fastening screw 238a, first thermally and electrically insulative washer 144a, electrically and thermally insulative sleeve 146a, thermally conductive blade substrate 170, electrically insulative layer 160, first blade heater contact pad 164a, first electrically conductive adhesive layer 216a, first distal power lead electrical contact pad 195a, first support arm flexible circuit substrate 212a, first thermally insulative spacer 62a, distal end of first thermally conductive blade support arm 131a, first and electrically insulative washer 214a, distal end of first electrically insulative flexible extension tab substrate 200a, first distal sense lead electrical contact pad 202a disposed on distal end of first electrically insulative flexible extension tab substrate 200a and first mechanical fastening nut 220a threaded onto first electrically conductive fastening screw 238a. Referring to both symmetrical braches seen, in part, in FIGS. 26 and 27, electrical communication between the first and second distal sense lead electrical contact pads, 202a, 202b, and sense leads, 198a, 198b, is provided by first and second sense lead extensions, 199a, 199b, disposed on first and second electrically insulative extension tabs, 210a, 210b, respectively (wherein first distal sense lead electrical contact pads 202a, sense lead 198a, first sense lead extensions 199a and first electrically insulative extension tabs 210a not shown since only the second branch of four-conductor flexible circuit 236b in seen in FIG. 26).

By way of example and without limitation and referring to FIGS. 23 through 29, four-conductor flexible circuit 230 comprising first and second power leads 196a and 196b, first and second power lead contact pads 207a and 207b, first and second distal power lead electrical contact pads 195a and 195b, first and second sense leads 198a and 198b, first and second sense lead contact pads 209a and 209b, first and second distal sense lead electrical contact pads 202a and 202b may be fabricated by adhesively bonding thin copper foil, having a thickness in the range from 0.0007 inch to 0.0028 inch, to a flexible electrically insulative polyimide substrate 150 such as Kapton (DuPont, Wilmington, Del.) having a thickness in the range from 0.001 inch to 0.004 inch. Photolithography is then used to selectively chemically etch and remove certain portions of the adhesively bonded copper on a flexible polyimide substrate to provide a preferred electrically conductive lead pattern as seen in FIGS. 23 through 29. Based on a copper lead thickness of 0.0014 inch, the widths of each of first and second power leads 196a and 196b in the first and second branches of the four-conductor flexible circuit preferably range from 0.045 to 0.055 as seen in FIG. 25. Based on a copper lead thickness of 0.0014 inch, the widths of each of first and second sense leads 198a and 198b in first and second braches of the four-conductor flexible circuit 236a and 236b preferably range from 0.010 to 0.015 as seen in FIG. 25. As seen in FIG. 29, electrically conductive adhesive layer 216a may be a high-temperature electrically conductive adhesive, by way of example but not limitation, an adhesive such as EPO-TEK H20E supplied by Epoxy Technology, Inc., Billerica, Mass.

Yet another embodiment of the present disclosure is seen wherein the first and second electrically conductive fastening screws 238a and 238b enable electrical communication with soft tissue 224 through direct electrical contact with soft tissue 224 as seen in FIG. 27, thereby enabling [a] the measurement of electrical impedance of soft tissue 224 located between first and second electrically conductive fastening screws 238a and 238b, such as to identify when maximum tissue impedance has been achieved (the screws act as electrodes) and/or [b] the conduction of high frequency current through soft tissue 224 to effect resistive heating of the underlying tissue. This method of tissue heating by the passage of high frequency current directly through tissue is commonly known as bipolar electrosurgical heating and typically employs a high-frequency current whose frequency is at least 100 kilohertz and often, but not limited to, a frequency of less than 6 megahertz. In regard to bipolar heating of tissue, refer to U.S. Pat. No. 5,891,142, which is incorporated herein by reference. Bipolar electrosurgical heating of soft tissue 224, as described above, may be employed in combination with a heatable blade 30 employing one of the heating element designs seen in FIGS. 19-22 (e.g., operating at a nominal blade temperature of 250° C. using one of the aforementioned temperature feedback control mechanisms) or may be employed with a cold surgical blade to effect all of the necessary heating of the underlying tissue necessary to achieve the sealing of severed blood vessels and associated hemostasis.

The range of dimensions for components of tissue excision system 10, as seen in FIGS. 4, 5, 7, 9, 11, 12B, 12C, 12D, 12E, 15, 16, 17, 18, 19, 20, 21, 22, and 27 are summarized below in units of inches unless specified otherwise:

$L1 = 0.08$ to $0.35$
$L2 = 0.35$ to $1.60$
$L3 = 0.01$ to $0.05$
$L4 = 0.10$ to $0.35$
$L5 = 5.6$ to $14.0$
$L6 = 2.5$ to $6.0$
$L7 = 0.30$ to $0.85$
$L8 = 0.30$ to $0.85$
$W1 = 0.03$ to $0.15$
$W2 = 0.10$ to $0.30$
$W3 = 0.15$ to $0.35$
$W4 = 0.30$ to $0.60$
$W5 = 0.30$ to $1.50$
$W6 = 0.30$ to $0.60$
$W7 = 0.20$ to $0.60$
$W8 = 0.10$ to $0.35$
$W9 = 0.03$ to $0.15$
$W10 = 0.04$ to $0.16$
$t1 = 0.02$ to $0.10$
$t2 = 0.0002$ to $0.005$
$t3 = 0.0001$ to $0.005$
$t4 = 0.02$ to $0.10$
$t5 = 0.0001$ to $0.005$
$t6 = 0.02$ to $0.10$
$t7 = 0.02$ to $0.10$
$t8 = 0.0001$ to $0.010$
$t9 = 0.0002$ to $0.003$
$t10 = 0.04$ to $0.15$
$t11 = 0.04$ to $0.15$
$t12 = 0.04$ to $0.15$
$t13 = 0.02$ to $0.10$
$t14 = 0.03$ to $0.30$
$T1 = 70$ to $600$ C
$T2 = 70$ to $600$ C
$N1 = 0.5$ to $5.0$ seconds
$\phi 1 = 15$ to $35$ degrees
$\phi 2 = 35$ to $60$ degrees The method for incising soft tissue while minimizing bleeding utilizing the preferred embodiments of the present disclosure is disclosed in connection with FIGS. 1 through 29 is set forth in the flow chart represented in FIGS. 30A and 30B. Those figures should be considered as labeled thereon. Looking first to FIGS. 1 and 30A, the surgical procedure commences as described at block 240 and arrow 242. A first step requires that controller 12 be turned to "ON" position using on/off power switch 39 and, using set-point temperature increase and decrease control switches 43, 41, and screen display 45, select set-point temperature, T1, for incision of soft tissue or, alternatively, using pre-determined default set point temperature (e.g., 250° C.) as described at block 244 and arrow 246. Next, removably attachable connector 38 located at proximal end of handpiece cable 36 is connected to first receptacle 37 on front panel of controller 12, as described at block 248 and arrow 250. Next, removably attachable connector 24 located at proximal end of footpedal cable 22 is connected to second receptacle 23 on front panel of controller 12, as described at block 252 and arrow 254.

Still referring to FIGS. 1 and 30A, controller 12 then automatically initiates pre-programmed self-test of operating system, as well as self-test of electrical connections to handpiece 14 and footpedal 16, as described at block 256 and arrow 258. Controller 12 then determines if electrical connections to handpiece 14 and footpedal 16 are confirmed, as described at block 260. If electrical connections between handpiece 14 and/or footpedal 16 and controller 12 are not confirmed, then a connection fault for the handpiece 14 and/or footpedal 16 is indicated on display screen 45 of controller 12 requiring operator to repeat steps for attaching removably attachable connector at proximal end of handpiece cable 38 and/or removably attachable connector at proximal end of footpedal cable 24 to first and second receptacles 37 and 23, respectively, at front panel of controller 12 as described at arrow 276, block 278 and arrow 277. However, if electrical connections between handpiece 14 and/or footpedal 16 and controller 12 are confirmed, then controller 12 initiates pre-programmed test of electrical resistance of heater disposed on heatable blade 30, as described at arrow 262, block 264 and arrow 266. If electrical resistance of heater disposed on heatable blade 30 is not within pre-determined electrical resistance range, then a heater resistance fault is indicated on display screen 45, as well as directive to replace faulty handpiece 14, as described at arrow 280, block 282 and arrow 284. However, if electrical resistance of heater disposed on heatable blade 30 is within pre-determined electrical resistance range, then controller 12 indicates "Position Heatable Cutting Blade in Preparation for Tissue Incision" on display screen 45 as described at block 272 and arrow 274.

Referring next to FIGS. 1 and 30B, operator depresses first pedal 18 of footpedal 16 labeled "Cut" and waits for a period of several seconds until audible intermittent tone issued by controller 12 becomes a continuous audible tone indicating that heatable blade 30 has reached selected or default "Cut" temperature, T1, as described at block 286 and arrow 288. Operator then positions heatable blade 30 at surgical site and proceeds to initiate and complete intended incision of soft tissue with heatable blade 30 at distal end of handpiece 14 while continuing to depress first pedal 18 of footpedal 16 and operator releases first pedal 18 of footpedal 16 to suspend power application to heatable blade 30, as described at block 290 and arrow 292. Advantageously, referring momentarily to FIGS. 2 and 16, the operator may manipulate handle 34 to orient the angle of straight cutting edge 189 relative to the direction of cutting 191 at an angle of between about 15 and 30 degrees relative to the direction of the forward direction to reduce the force required for soft tissue excision. Operator next visually examines site of completed tissue incision to observe whether there is any residual bleeding occurring from transected blood vessels, as described at block 294. If there is no visually observable bleeding from transected blood vessels at site of completed tissue excision, then surgical procedure is complete and handpiece 14 is removed from surgical site, as described at arrow 298 and block 300.

Referring to FIGS. 1 and 30B, if there is visually observable bleeding from transected blood vessels at site of completed tissue excision, then operator depresses second pedal 20 labeled "Coag" of footpedal 16 and waits for a period of several seconds until audible intermittent tone issued by controller 12 becomes a continuous audible tone indicating that heatable blade 30 has reached selected or default "Coag" temperature, T2, as described at arrow 296, block 302 and arrow 304.

Referring now to FIGS. 1, 27 and 30B, operator determines if controller 12 and handpiece 14 include capability to measure electrical impedance of soft tissue 224 in region underlying plane of incision as seen in FIG. 27, as described at block 310. If controller 12 and handpiece 14 do include capability to measure electrical impedance of soft tissue 224 in region underlying plane of incision, as seen in FIG. 27, then operator positions heatable blade 30 at site of visually observable bleeding from transected blood vessels and proceeds to apply tamponade with distal face of heatable blade 30 to tissue (as seen at arrow 312 and block 307) and simultaneously listens for decrease in frequency of audible tone and attainment of a continuous lower frequency audible tone issued by controller 12 during period while simultaneously applying heat to soft tissue 224 using heatable blade 30 operating at "Coag" temperature, T2, to seal any blood vessels not previously sealed during the soft tissue incision step, as described at arrow 313 and block 318. If frequency of audible tone issued by controller 12 detected by operator continues to decrease, the operator continues to depress second pedal 20 labeled "Coag" of footpedal 16, as described at arrow 322, block 324 and returning via arrow 326 to block 318. If frequency of audible tone issued by controller 12 detected by operator is no longer continuing to decrease, but is audibly constant, the operator releases second pedal 20 labeled "Coag" of footpedal 16 and removes heatable blade 30 from tissue incision site since surgical procedure is complete, as described at arrow 320 and block 328.

Still referring now to FIGS. 1, 27 and 30B, if controller 12 and handpiece 14 does not include capability to measure electrical impedance of soft tissue 224 in region underlying plane of incision (as seen in FIG. 27), then operator positions heatable blade 30 at site of visually observable bleeding from transected blood vessels and proceeds to apply tamponade with distal face of heatable blade 30 to soft tissue 224 while simultaneously applying heat to tissue for a period of N1 seconds to seal any blood vessels not previously sealed during the soft tissue incision step followed by the release of second footpedal 20 by operator to suspend power application to heatable blade 30, as described at arrow 308 and block 306. At the end of heat and tamponade application duration of N1 seconds, surgical procedure is complete, as described at arrow 314 and block 316.

While the apparatus, system, and method have been described with reference to various embodiments, those skilled in the art will understand that various changes may be made and equivalents may be substituted for elements thereof without departing from the scope and essence of the disclosure. In addition, many modifications may be made to adapt a particular situation or material in accordance with the teachings of the disclosure without departing from the essential scope thereof. Therefore, it is intended that the disclosure not be limited to the particular embodiments disclosed, but that the disclosure will include all embodiments falling within the scope of the appended claims. In this application all units are in the US engineering system, unless otherwise expressly indicated. Also, all citations referred herein are expressly incorporated herein by reference.

We claim:

1. An apparatus for excision of soft tissue using a mechanically sharp blade with concurrent heating to effect tissue incision with minimal bleeding applied to surgical adenoidectomy and tonsillectomy, comprising:
   (a) a handle (34);
   (b) an elongated blade support member (32) having a distal end and a proximal end, and extending from the handle and comprising;
      (i) a first electrically and thermally conductive blade support shank (50),
      (ii) a second electrically and thermally conductive blade support shank (52),
      (iii) and an intervening electrical insulative spacer (56) that electrically isolates the first electrically and thermally conductive blade support shank (50) from the second electrically and thermally conductive blade support shank (52);
   (c) a first electrically and thermally conductive blade support arm (51) having a distal end incorporating a threaded hole (55a) and extending from the first electrically and thermally conductive blade support shank (50), and having an electrical contact surface;
(d) a second electrically and thermally conductive blade support arm (53) having a distal end incorporating a threaded hole (55*b*) and extending from the second electrically and thermally conductive blade support shank (52), and having an electrical contact surface;
(e) a surgically sharp heatable blade (30) having a cutting edge comprising a thermally conductive blade substrate (170), a first layer of electrically insulative material (160) onto which is disposed a second layer of electrically resistive material (162), and a first and second blade heater contact pads (164*a* and 164*b*), the surgically sharp heatable blade being mechanically fastened:
  (i) to the first electrically and thermally conductive blade support arm (51) with an intervening first thermally and electrically insulative spacer (62*a*) and first fastening screw (72*a*), a first electrically and thermally insulative sleeve (76*a*) surrounding any exposed portion of the first fastening screw, and a first electrically and thermally insulative washer (74*a*) positioned between the first fastening screw and the surgically sharp heatable blade; and
  (ii) to a second electrically and thermally conductive blade support arm with an intervening second thermally and electrically insulative spacer (62*b*) and a second fastening screw (72*b*), a second electrically and thermally insulative sleeve (76*b*) surrounding any exposed portion of the second fastening screw, and a second electrically and thermally insulative washer (74*b*) positioned between the second fastening screw and the surgically sharp heatable blade;
the first thermally and electrically insulative spacer surmounted by first and third electrical contact pads (64*a*) and being in electrical communication by a first copper plated via (66*a*);
the second thermally and electrically insulative spacer surmounted by second and fourth electrical contact pads (64*b*), being in electrical communication by a second copper plated via (66*b*);
the first and second electrical contact pads on the first and second thermally and electrically insulative spacers being in electrical communication with the first and second blade heater contact pads;
the third and fourth electrical contact pads on the first and second thermally and electrically insulative spacers being in electrical communication with the corresponding electrical contact surfaces on the first and second electrically and thermally conductive support arms, respectively;
(f) a first electrically conductive lead (81*a*) in electrical communication with and fastened to the first electrically and thermally conductive blade support shank;
(g) a second electrically conductive lead (81*b*) in electrical communication with and fastened to the second electrically and thermally conductive blade support shank; and
(h) a controller, wherein the first and second electrically conductive leads extend from the proximal ends of first and second electrically and thermally conductive blade support shanks of the thermally conductive blade support member to the controller.

2. The apparatus of claim 1, wherein the heatable blade has at least one straight cutting edge for excising soft tissue.

3. The apparatus of claim 1, wherein the heatable blade has at least one triangular shaped cutting edge for excising soft tissue.

4. The apparatus of claim 1, wherein the heatable blade has an electrically conductive heating element that incorporates a conductive material having a high temperature coefficient of resistance of at least 400 ppm per degree C.

5. The apparatus of claim 1, wherein the heatable blade has at least one cutting edge having a tip, wherein the heatable blade is covered with a non-stick coating except at the cutting edge tip.

6. The apparatus of claim 1, wherein the elongated blade support member is malleable.

7. The apparatus of claim 1, wherein first and second thermal barrier members are positioned between the heatable blade and the first and second distal ends of the electrically and thermally conductive blade support arms, respectively, to reduce conduction of heat.

8. The apparatus of claim 1, wherein the heated blade operates at a temperature in the range from about 150 C to 250 C.

9. The apparatus of claim 1, wherein the first electrically and thermally conductive blade support shank is one-piece and integral with the first electrically and thermally conductive support arm has a thermal conductivity of at least 1.5 watts/cm-C.

10. The apparatus of claim 1, wherein the second electrically and thermally conductive blade support shank is one-piece and integral with the second electrically and thermally conductive support arm has a thermal conductivity of at least 1.5 watts/cm-C.

11. The apparatus of claim 1, wherein the width (W1) of first and second electrically and thermally conductive blade support arms is in the range from 0.030" to 0.100".

12. The apparatus of claim 1, wherein the thickness (t10) of first and second electrically and thermally conductive blade support arms is in the range from 0.040" to 0.150".

13. The apparatus of claim 1, wherein thermally conductive blade substrate is martensitic stainless steel heat treated to hardness of at least 58 Rockwell C.

14. The apparatus of claim 1, wherein the first and second electrically and thermally conductive blade support arms have integral support shaft members, the maximum temperature of the exposed surfaces of the electrically and thermally conductive blade support arms and their respective integral support shaft members is 50 C or lower during the expected exposure duration associated with an excision and coagulation procedure thereby avoiding unwanted thermal injury to surrounding healthy tissue.

* * * * *